(12) United States Patent
DelMain et al.

(10) Patent No.: US 8,050,297 B2
(45) Date of Patent: Nov. 1, 2011

(54) SYSTEM AND METHOD FOR SHARING A COMMON COMMUNICATION CHANNEL BETWEEN MULTIPLE SYSTEMS OF IMPLANTABLE MEDICAL DEVICES

(75) Inventors: Gregory J. DelMain, Minnetrista, MN (US); Dan Folkman, Ra'anana (IL); Paul DeRocco, Pacific Palisades, CA (US); Lawrence J. Karr, Santa Monica, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 547 days.

(21) Appl. No.: 12/157,652

(22) Filed: Jun. 12, 2008

(65) Prior Publication Data

US 2008/0255636 A1  Oct. 16, 2008

Related U.S. Application Data

(62) Division of application No. 10/866,209, filed on Jun. 10, 2004, now Pat. No. 7,406,105.

(60) Provisional application No. 60/550,248, filed on Mar. 3, 2004.

(51) Int. Cl.
*H04J 3/06* (2006.01)

(52) U.S. Cl. ...... 370/514; 370/512; 455/41.1; 455/41.2; 455/41.3; 128/899

(58) Field of Classification Search .................. 370/514, 370/509, 510, 512; 455/41.1, 41.2, 41.3; 128/899
See application file for complete search history.

(56) References Cited

U.S. PATENT DOCUMENTS 6,958,677 B1 * 10/2005 Carter .......................... 340/10.1
2002/0141356 A1 * 10/2002 Beidas et al. ................. 370/324
* cited by examiner

*Primary Examiner* — Luat Phung
(74) *Attorney, Agent, or Firm* — Oleh J. Zajac

(57) ABSTRACT

A system and method that facilitates multiple systems of communicating devices, i.e., a master device and one or more implantable slave devices, to coexist on a common, e.g., RF, communication channel having a limited temporal bandwidth while maintaining the required update rate between each master device and its associated slave devices. In embodiments of the present invention, master devices periodically transmit one or more beacon messages that are suitable for identification by other such master devices at a communication range greater than the communication range that may cause interference between systems and thus enabling one or more systems to cause the position of its frame periods to be interleaved with the frame periods of other such systems in anticipation of systems moving in closer proximity and actually interfering with each other.

10 Claims, 35 Drawing Sheets

OPEN LOOP CONTROL/MONITOR

CLOSED LOOP CONTROL

EXEMPLARY INJURY

COORDINATED CLOSED LOOP HAND CONTROL

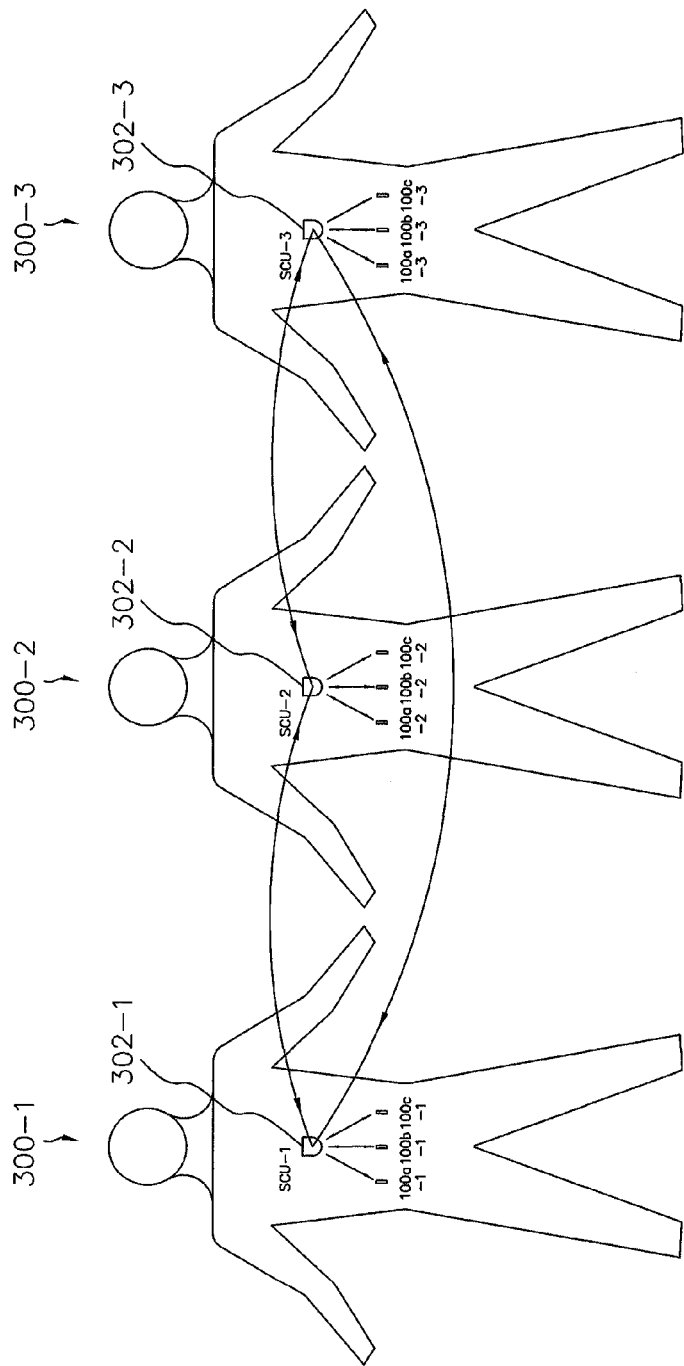
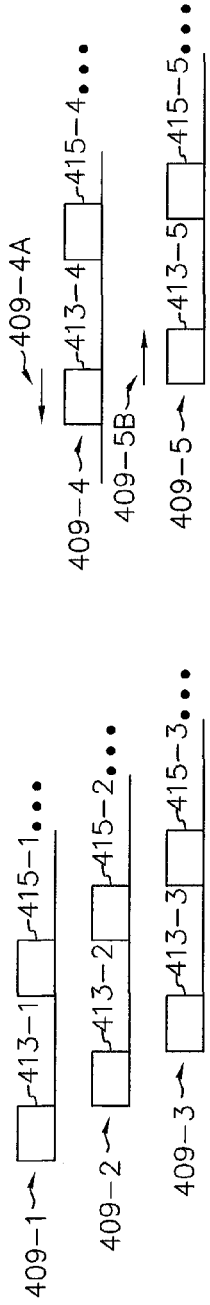
FIG. 9A
FIG. 9B
FIG. 9C

| Location | 1<br>1717 | 2<br>1620 | 3<br>1522 | 4<br>1423 | 5<br>1323 | 6<br>1222 | 7<br>1120 | 8<br>1017 | 9<br>913 | 10<br>808 | 11<br>702 | 12<br>595 | 13<br>487 | 14<br>378 | 15<br>268 | 16<br>157 |
|---|---|---|---|---|---|---|---|---|---|---|---|---|---|---|---|---|
| 1<br>1717 | X | 97 | 195 | 294 | 394 | 495 | 597 | 700 | 804 | 909 | 1015 | 1122 | 1230 | 1339 | 1449 | 1560 |
| 2<br>1620 | 97 | X | 98 | 197 | 297 | 398 | 500 | 603 | 707 | 812 | 918 | 1025 | 1133 | 1242 | 1352 | 1463 |
| 3<br>1522 | 195 | 98 | X | 99 | 199 | 300 | 402 | 505 | 609 | 714 | 820 | 927 | 1035 | 1144 | 1254 | 1365 |
| 4<br>1423 | 294 | 197 | 99 | X | 100 | 201 | 303 | 406 | 510 | 615 | 721 | 828 | 936 | 1045 | 1155 | 1266 |
| 5<br>1323 | 394 | 297 | 199 | 100 | X | 101 | 203 | 306 | 410 | 515 | 621 | 728 | 836 | 945 | 1055 | 1166 |
| 6<br>1222 | 495 | 398 | 300 | 201 | 101 | X | 102 | 205 | 309 | 414 | 520 | 627 | 735 | 844 | 954 | 1065 |
| 7<br>1120 | 597 | 500 | 402 | 303 | 203 | 102 | X | 103 | 207 | 312 | 418 | 525 | 633 | 742 | 852 | 963 |
| 8<br>1017 | 700 | 603 | 505 | 406 | 306 | 205 | 103 | X | 104 | 209 | 315 | 422 | 530 | 639 | 749 | 860 |
| 9<br>913 | 804 | 707 | 609 | 510 | 410 | 309 | 207 | 104 | X | 105 | 211 | 318 | 426 | 535 | 645 | 756 |
| 10<br>808 | 909 | 812 | 714 | 615 | 515 | 414 | 312 | 209 | 105 | X | 106 | 213 | 321 | 430 | 540 | 651 |
| 11<br>702 | 1015 | 918 | 820 | 721 | 621 | 520 | 418 | 315 | 211 | 106 | X | 107 | 215 | 324 | 434 | 545 |
| 12<br>595 | 1122 | 1025 | 927 | 828 | 728 | 627 | 525 | 422 | 318 | 213 | 107 | X | 108 | 217 | 327 | 438 |
| 13<br>487 | 1230 | 1133 | 1035 | 936 | 836 | 735 | 633 | 530 | 426 | 321 | 215 | 108 | X | 109 | 219 | 330 |
| 14<br>378 | 1339 | 1242 | 1144 | 1045 | 945 | 844 | 742 | 639 | 535 | 430 | 324 | 217 | 109 | X | 110 | 221 |
| 15<br>268 | 1449 | 1352 | 1254 | 1155 | 1055 | 954 | 852 | 749 | 645 | 540 | 434 | 327 | 219 | 110 | X | 111 |
| 16<br>157 | 1560 | 1463 | 1365 | 1266 | 1166 | 1065 | 963 | 860 | 756 | 651 | 545 | 438 | 330 | 221 | 111 | X |

FIG. 11

| Table Index | Absolute Value of Difference Between Wandering Beacons | Offset From Header Start of Lowest Offset Clocked Value |
|---|---|---|
| 0 | 97 | 1620 |
| 1 | 98 | 1522 |
| 2 | 99 | 1423 |
| 3 | 100 | 1323 |
| 4 | 101 | 1222 |
| 5 | 102 | 1120 |
| 6 | 103 | 1017 |
| 7 | 104 | 913 |
| 8 | 105 | 808 |
| 9 | 106 | 702 |
| 10 | 107 | 595 |
| 11 | 108 | 487 |
| 12 | 109 | 378 |
| 13 | 110 | 268 |
| 14 | 111 | 157 |
| 15 | 195 | 1522 |
| 16 | 197 | 1423 |
| 17 | 199 | 1323 |
| 18 | 201 | 1222 |
| 19 | 203 | 1120 |
| 20 | 205 | 1017 |
| 21 | 207 | 913 |
| 22 | 209 | 808 |
| 23 | 211 | 702 |
| 24 | 213 | 595 |
| 25 | 215 | 487 |
| 26 | 217 | 378 |
| 27 | 219 | 268 |
| 28 | 221 | 157 |
| 29 | 294 | 1423 |
| 30 | 297 | 1323 |
| 31 | 300 | 1222 |
| 32 | 303 | 1120 |
| 33 | 306 | 1017 |
| 34 | 309 | 913 |
| 35 | 312 | 808 |
| 36 | 315 | 702 |
| 37 | 318 | 595 |
| 38 | 321 | 487 |
| 39 | 324 | 378 |
| 40 | 327 | 268 |
| 41 | 330 | 157 |
| 42 | 394 | 1323 |

FIG. 12-1

| Table Index | Absolute Value of Difference Between Wandering Beacons | Offset From Header Start of Lowest Offset Clocked Value |
|---|---|---|
| 43 | 398 | 1222 |
| 44 | 402 | 1120 |
| 45 | 406 | 1017 |
| 46 | 410 | 913 |
| 47 | 414 | 808 |
| 48 | 418 | 702 |
| 49 | 422 | 595 |
| 50 | 426 | 487 |
| 51 | 430 | 378 |
| 52 | 434 | 268 |
| 53 | 438 | 157 |
| 54 | 495 | 1222 |
| 55 | 500 | 1120 |
| 56 | 505 | 1017 |
| 57 | 510 | 913 |
| 58 | 515 | 808 |
| 59 | 520 | 702 |
| 60 | 525 | 595 |
| 61 | 530 | 487 |
| 62 | 535 | 378 |
| 63 | 540 | 268 |
| 64 | 545 | 157 |
| 65 | 597 | 1120 |
| 66 | 603 | 1017 |
| 67 | 609 | 913 |
| 68 | 615 | 808 |
| 69 | 621 | 702 |
| 70 | 627 | 595 |
| 71 | 633 | 487 |
| 72 | 639 | 378 |
| 73 | 645 | 268 |
| 74 | 651 | 157 |
| 75 | 700 | 1017 |
| 76 | 707 | 913 |
| 77 | 714 | 808 |
| 78 | 721 | 702 |
| 79 | 728 | 595 |
| 80 | 735 | 487 |
| 81 | 742 | 378 |
| 82 | 749 | 268 |
| 83 | 756 | 157 |
| 84 | 804 | 913 |
| 85 | 812 | 808 |
| 86 | 820 | 702 |

FIG. 12-2

| Table Index | Absolute Value of Difference Between Wandering Beacons | Offset From Header Start of Lowest Offset Clocked Value |
|---|---|---|
| 87 | 828 | 595 |
| 88 | 836 | 487 |
| 89 | 844 | 378 |
| 90 | 852 | 268 |
| 91 | 860 | 157 |
| 92 | 909 | 808 |
| 93 | 918 | 702 |
| 94 | 927 | 595 |
| 95 | 936 | 487 |
| 96 | 945 | 378 |
| 97 | 954 | 268 |
| 98 | 963 | 157 |
| 99 | 1015 | 702 |
| 100 | 1025 | 595 |
| 101 | 1035 | 487 |
| 102 | 1045 | 378 |
| 103 | 1055 | 268 |
| 104 | 1065 | 157 |
| 105 | 1122 | 595 |
| 106 | 1133 | 487 |
| 107 | 1144 | 378 |
| 108 | 1155 | 268 |
| 109 | 1166 | 157 |
| 110 | 1230 | 487 |
| 111 | 1242 | 378 |
| 112 | 1254 | 268 |
| 113 | 1266 | 157 |
| 114 | 1339 | 378 |
| 115 | 1352 | 268 |
| 116 | 1365 | 157 |
| 117 | 1449 | 268 |
| 118 | 1463 | 157 |
| 119 | 1560 | 157 |

FIG. 12-3

| Table Index | Offset From Header Start of Lowest Offset Clocked Value |
|---|---|
| 0 | ------ |
| • | ------ |
| • | ------ |
| • | ------ |
| 96 | ------ |
| 97 | 1620 |
| 98 | 1522 |
| 99 | 1423 |
| 100 | 1323 |
| 101 | 1222 |
| 102 | 1120 |
| 103 | 1017 |
| 104 | 913 |
| 105 | 808 |
| 106 | 702 |
| 107 | 595 |
| 108 | 487 |
| 109 | 378 |
| 110 | 268 |
| 111 | 157 |
| 112 | ------ |
| • | ------ |
| • | ------ |
| • | ------ |
| 195 | 1522 |
| 196 | ------ |
| 197 | 1423 |
| 198 | ------ |
| 199 | 1323 |
| 200 | ------ |
| 201 | 1222 |
| 202 | ------ |
| 203 | 1120 |
| 204 | ------ |
| 205 | 1017 |
| 206 | ------ |
| 207 | 913 |
| 209 | 808 |
| 210 | ------ |
| 211 | 702 |
| 212 | ------ |
| • | ------ |
| • | ------ |
| • | ------ |
| 1559 | ------ |
| 1560 | 157 |

FIG. 13

| 7 | | | | | | | 0 |
|---|---|---|---|---|---|---|---|
| X | X | X | X | X | OL | LV | DC |

FIG. 28

| | Procedure | Procedure name | Calling software | Executing software | Outgoing vector | Outgoing / Incoming Parameters |
|---|---|---|---|---|---|---|
| 1 | Local master move | A. Ready_Move<br>B. Ready_Move_Complete<br>C. Execute_Move<br>D. Move_Complete | MTM<br>MCU<br>MTM<br>MCU | MCU<br>MCU<br>MCU<br>MCU | Load_BION<br>Move_Readiness<br>Execute_Move<br>Move_Complete | Load_BION=1<br>Move_Readiness=1<br>Offset<br>Move_complete=1 |
| 2 | Local master beaconing | Beacon_Setup | MTM | MCU | Beacon_Code<br>ID_Number<br>WACK<br>TACK<br>BION_slots | |
| 3 | DB update after move | Database_Move_Update | MTM | MCU | Execute_Move | Offset |
| 4 | Database update | Database_Update | MCU | MCU | | |
| 5 | Occupied slots update | Local_Slots | MTM | MTM | Local_slots=1 | Occupied Slots |
| 6 | Reset FC and OSC | Reset_FC_OSC | MCU | MTM | Reset_FC_OSC=1 | |
| 7 | Read FC, OSC, start | Read_FC_OSC_start | MCU | MTM | Read_FC_OSC=1 | FC, Drifting_Bauds |

SYSTEM AND METHOD FOR SHARING A COMMON COMMUNICATION CHANNEL BETWEEN MULTIPLE SYSTEMS OF IMPLANTABLE MEDICAL DEVICES

This application is a divisional of U.S. application Ser. No. 10/866,209, filed Jun. 10, 2004, issued as U.S. Pat. No. 7,406,105, and this application claims the benefit of U.S. Provisional Application No. 60/550,248, filed Mar. 3, 2004.

FIELD OF THE INVENTION

The present invention is generally directed to systems of implantable medical devices and in particular to such systems that communicate with each other over a common communication channel and solutions to allow such systems to operate essentially independently of other such systems which also operate over the common communication channel.

BACKGROUND OF THE INVENTION

The present invention generally relates to systems for monitoring and/or affecting parameters of a patient's body for the purpose of medical diagnosis and/or treatment. More particularly, such systems are characterized by a plurality of devices, preferably battery powered, configured for implanting within a patient's body, each device being configured to sense a body parameter, e.g., temperature, $O_2$ content, physical position, electrical potential, etc., and/or to affect a parameter, e.g., via nerve and/or muscle stimulation.

Commonly owned U.S. Pat. No. 6,164,284 entitled "System of Implantable Devices For Monitoring and/or Affecting Body Parameters" and U.S. Pat. No. 6,185,452 entitled "Battery Powered Patient Implantable Device", each incorporated herein by reference in their entirety, describe devices configured for implantation within a patient's body, i.e., beneath a patient's skin, for performing various functions including: (1) stimulation of body tissue and/or sensing of body parameters, and (2) communicating between implanted devices and devices external to a patient's body. Depending upon the ailment affecting the patient, it may be desirable to communicate with a number of different devices, e.g., from one to thousands, while maintaining an update rate, e.g., on the order of every 1 millisecond to every second, sufficient to control and/or monitor the body parameter(s) at issue. Commonly owned U.S. Pat. No. 6,472,991 entitled "Multichannel Communication Protocol Configured To Extend The Battery Life Of An Implantable Device", incorporated herein by reference in its entirety, describes an exemplary communication protocol for communicating between a master device (referred to as a system control unit (SCU) in the referenced patent) which may be implanted or in proximity to a patient that communicates with a plurality of slave devices, preferably implantable, across a common communication channel during a frame period, preferably of fixed duration. The frame periods are essentially sequential and temporally contiguous and as such there is only one repeatable frame period available that occupies the entire temporal bandwidth of the common communication channel. Fortunately, while this exemplary communication protocol allocates time slots for a large number of implantable slave devices, most systems will not be populated to that predefined maximum amount. This allows for a gap within the frame period that is specified relating to the actual number of implantable slave devices in the system or the system configuration. Unfortunately, when multiple systems of devices, i.e., a master device and associated slave devices, are in close proximity, i.e., within an interference communication range of each other, interference between the master or slave devices in different systems may cause one or more devices or systems to perform improperly since there is a statistical probability that two or more devices may transmit during the same or overlapping time slots and consequently result in difficulty in receiving by individual receivers. Accordingly, the present invention is directed to a system and method that facilitate multiple systems to coexist on a common communication channel while maintaining the required update rate.

SUMMARY OF THE INVENTION

The present invention is directed to a system and method that facilitates multiple systems of communicating devices, i.e., a master device and one or more implantable slave devices, to coexist on a common communication channel having a limited temporal bandwidth while maintaining the required update rate between each master device and its associated slave devices. The system and method of the present invention is particularly useful in a system comprised of a master device (also referred to as a system control unit (SCU)) and one or more slave devices implanted in the patient's body, i.e., within the envelope defined by the patient's skin. Each such implanted device is configured to be monitored and/or controlled by the SCU via a wireless, e.g., RF, common communication channel.

In an exemplary environment, the SCU comprises a programmable unit capable of (1) transmitting commands to at least some of a plurality of implanted devices and (2) receiving data signals from at least some of those implanted devices. Preferably, the system operates in closed loop fashion whereby the commands transmitted by the SCU are dependent, in part, on the content of the data signals received by the SCU.

Each implanted device in this exemplary environment is configured similarly to the devices described in the commonly owned U.S. Pat. No. 6,164,284 and typically comprises a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between the SCU and the other implanted devices can be implemented in various ways, e.g., via a modulated sound signal, an AC magnetic field, an RF signal, a propagated electromagnetic wave, a light signal, or electrical conduction.

Preferably, such systems, i.e., a master device and one or more associated slave devices, repeatedly communicate with each other during sequential and temporally contiguous frame periods, preferably of fixed duration such that there is only one repeatable frame period available that occupies the entire temporal bandwidth of the common communication channel, e.g., over a common RF communication frequency. A preferred implementation of this exemplary communication protocol is described in commonly owned U.S. Pat. No. 6,472,991 entitled "Multichannel Communication Protocol Configured To Extend The Battery Life Of An Implantable Device", incorporated herein by reference in its entirety. Fortunately, while this exemplary communication protocol allocates time slots for a large number of implantable slave devices, most systems will not be populated to that predefined maximum amount. This allows for a temporal gap in the frame period that is specified relative to the actual number of implantable slave devices in the system or the mode of operation. Unfortunately, when multiple systems of devices, i.e., a master device and associates slave devices, are in close proximity, i.e., within an interference communication range of each other, interference between the master or slave devices in different systems may cause one or more devices or systems to perform improperly since there is a statistical probability that two or more devices may transmit during the same or overlapping time slots and consequently result in difficulty in receiving by individual receivers. Accordingly, the present invention is directed to a system and method that facilitate multiple systems to coexist on a common communication channel while maintaining the required update rate. In the present invention, this is accomplished by altering the start of the frame periods of one or more master devices and its associated slave devices according to a priority algorithm primarily based upon a unique identification code that is assigned to each master device. Preferably, master devices of the present invention are formed to have sufficient sensitivity to enable reception of beacon messages from other master devices such that this altering of the start of the frame periods will occur before any actual communication interference does occur. The resulting communications have each system's intra-system communication gap used for inter-system communications between other such systems.

In accordance with the present invention, a preferred method is described that enables a plurality of systems to cooperatively coexist on a common communication channel wherein each system is comprised of a master device having a unique identification code and one or more associated slave devices that communicate with said master device during periodic and essentially temporally contiguous frame periods determined by each master device and having occupied temporal portions of each frame period comprised of transmission communication periods dedicated to each master device and to each slave device and wherein each frame period has a start and an end that essentially spans the entire temporal bandwidth of the common communication channel, wherein the method comprises the steps of (1) transmitting a plurality of beacon message types during each frame period from each master device wherein each beacon message type has a unique beacon marker code portion and at least one beacon message type has a moveable temporal offset from the start of its respective frame period, (2) receiving beacon messages by the master devices from other master devices that are within communication range, (3) calculating the relative temporal displacement of the frame periods of other master devices according to the relative temporal offsets of one or more of the beacon messages to the start of the frame periods of said master devices, (4) determining whether at least one of said systems may interfere with communications of another one of said systems and accordingly calculating a new temporal placement for the frame period of a selected one of the systems according to the received beacon messages and the unique identification codes, and (5) causing the selected one of the systems comprised of a master device and one or more associated slave devices to temporally displace the start of its frame period to allow the occupied temporal portions of the selected one of the systems to be temporally interleaved with other occupied temporal portions of the systems on the common communication channel when said determining step has determined the potential for communication interference between two or more of said systems.

The novel features of the invention are set forth with particularity in the appended claims. The invention will be best understood from the following description when read in conjunction with the accompanying drawings.

BRIEF DESCRIPTION OF THE DRAWINGS

FIGS. 9A-9C show simplified diagrams of the interactions between a plurality of systems, i.e., SCUs and implantable devices, which are allowed to coexist in a restricted location in embodiments of the present invention. Specifically, FIG. 9B shows a timing diagram associated with a successfully interleaved, and thus non-interfering, group of three systems (as shown in FIG. 9A) while FIG. 9C shows a timing diagram of two partially overlapping systems that will interfere with each other should they attempt to coexist in close proximity.

FIG. 11 shows a matrix of the potential temporal differences between two different wandering beacons selected from a predefined set of beacon offset locations.

FIGS. 12-1 through 12-3 show tables that enumerate the correspondence between the temporal displacements of two wandering beacons and a temporal offset from the start of the frame period of a local master device to determine the start of the frame period of a remote master device and to correlate these differences to multiple remote master devices and their associated systems.

FIG. 13 shows a lookup table having that may be used to identify the frame period offset.

In FIG. 26, the remote master device's downlink is located within the local master device's downlink section while in FIG. 27, the remote master device's downlink exists in the local master device's uplink section.

FIG. 28 illustrates the structure of the 'status' field used in an exemplary implementation.

FIG. 31 illustrates the procedures used by the state machine in an exemplary implementation and FIG. 32 shows the associated data structures.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a system and method that facilitates multiple systems of communicating devices, i.e., a master device and one or more associated slave devices, to coexist on a common communication channel having a limited temporal bandwidth while maintaining the required update rate between each master device and its one or more associated slave devices. The system and method of the present invention is particularly useful in a system comprised of a master device (also referred to as a system control unit (SCU)) and one or more slave devices preferably implanted in the patient's body, i.e., within the envelope defined by the patient's skin. Each such implanted device is configured to be monitored and/or controlled by the SCU via a wireless common communication channel, e.g., over a common RF communication frequency via time division multiplexing (TDM).

In an exemplary environment, the SCU comprises a programmable unit capable of (1) transmitting commands to at least some of a plurality of implanted devices and (2) receiving data signals from at least some of those implanted devices. Preferably, the system operates, at least in part, in a closed loop fashion whereby the commands transmitted by the SCU are dependent, in part, on the content of the data signals received by the SCU.

Each implanted device in this exemplary environment is configured similarly to the devices described in the commonly owned U.S. Pat. No. 6,164,284 (hereinafter referred to as the '284 patent) and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Figure 1:
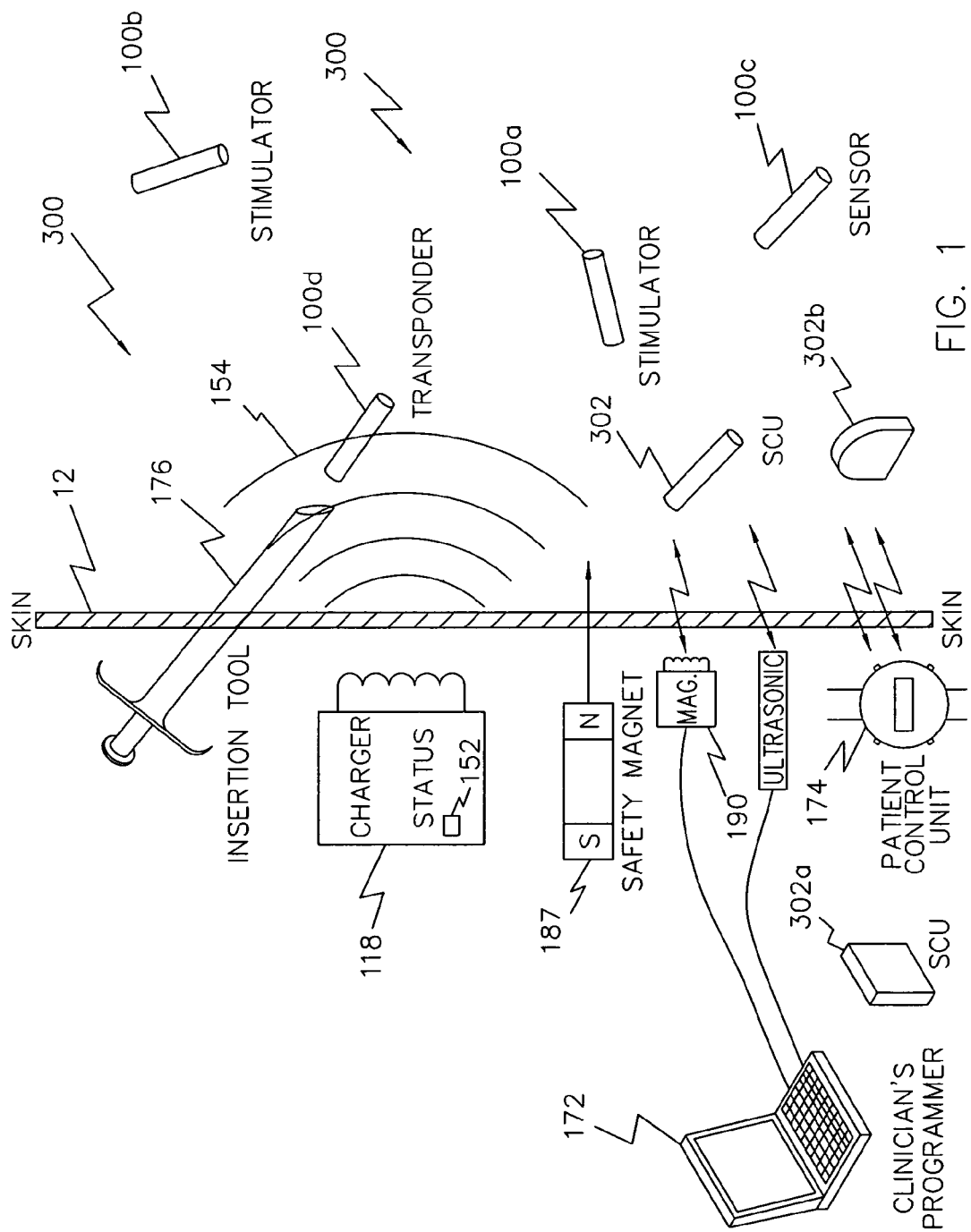
FIG. 1 is a simplified block diagram of an exemplary system suitable for practicing the enhanced communication protocol of the present invention, the system being comprised of implanted devices, e.g., microstimulators, microsensors and microtransponders, under control of a system control unit (SCU).
Figure 2:
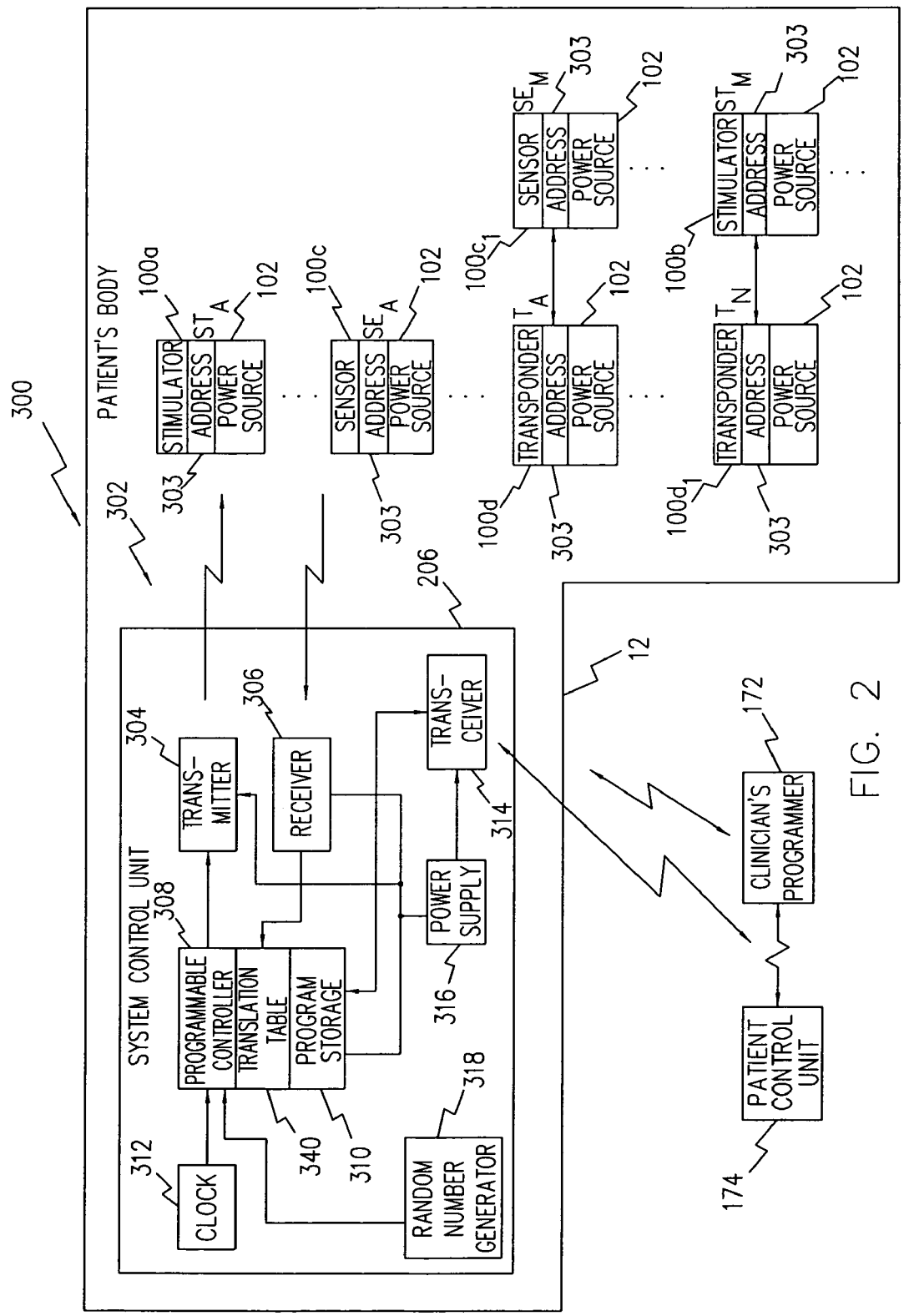
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with a unique address or identification code (ID) 303 specified in address storage circuitry 108 (see FIG. 3A) as described in the '284 patent. Unique is a relative term, e.g., the more bits used to specify the identification code the easier it will be to distinguish one device or, in the case of master devices, one system of devices from another system of devices. Accordingly, as used in this patent application, unique is only intended to specify that the ID 303 is distinguishable from the IDs of other devices that may exist within the same environment.

By using one or more such implantable devices in conjunction with the SCU 302, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5-7), the SCU 302 periodically interrogates one or more microsensors and accordingly adjusts the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body, e.g., as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be suitable for a potential communication channel. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication channel is used.

Figure 3A:
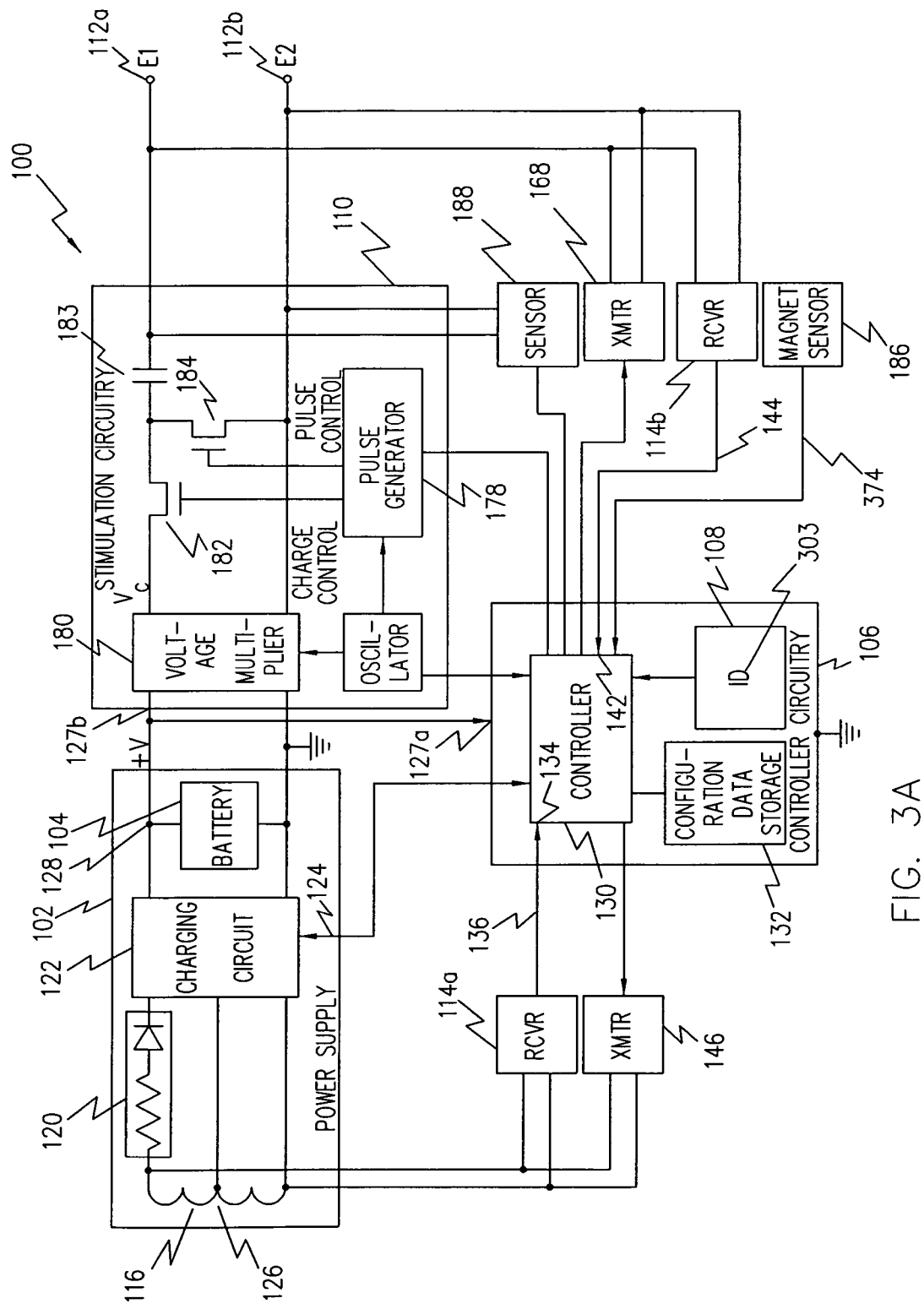
FIG. 3A comprises a block diagram of an exemplary implantable device, as shown in U.S. Pat. No. 6,164,284, including a battery for powering the device for a period of time in excess of one hour in response to a command from the system control unit. Embodiments of the present invention are particularly suited for handling communications between systems of such devices.
Figure 3B:
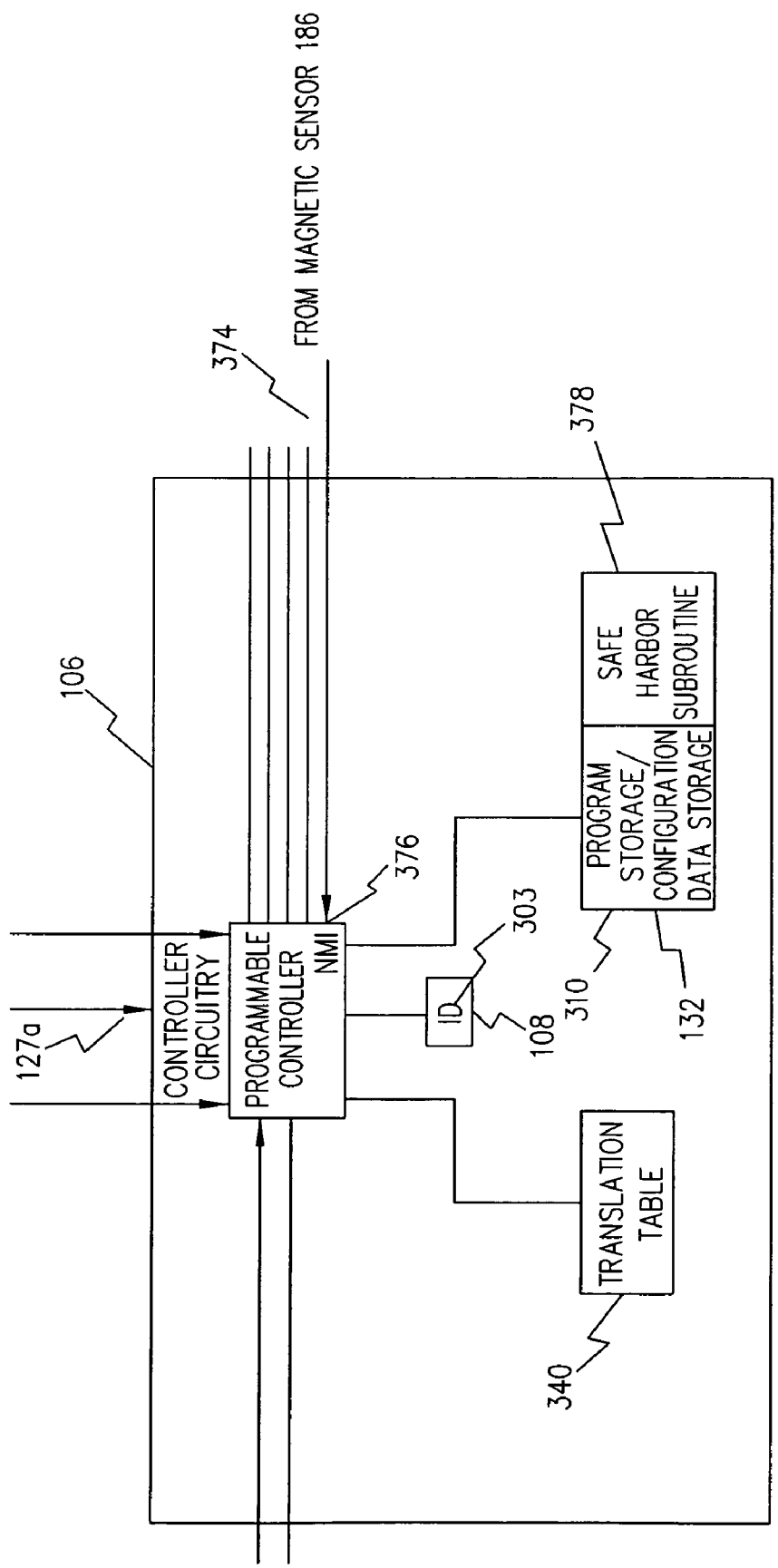
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote master device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

Preferably, the contents of the program storage 310, i.e., the software that controls the operation of the programmable controller 308, can be remotely downloaded, e.g., from the clinician's programmer 172 using data modulated onto an RF signal or an AC magnetic field. In this mode, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is particularly significant if multiple patients could be physically located, e.g., in adjoining beds, within the communication range of the clinician's programmer 172 as addressed by embodiments of the present invention described herein.

Preferably, the SCU 302 can operate for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, $O_2$ content, voltage, current, impedance, etc. and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
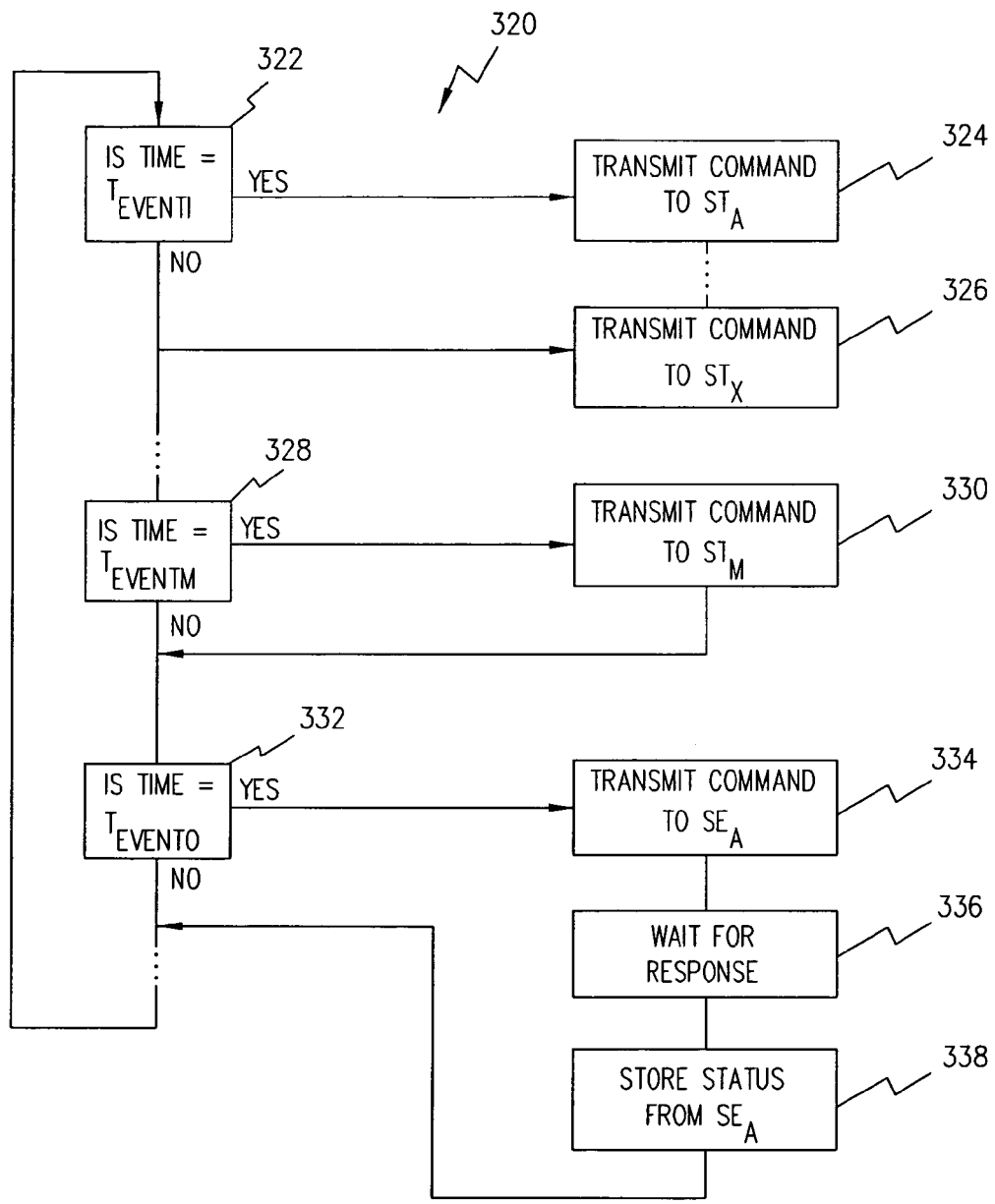
FIG. 4 shows an exemplary flow chart of the use of an exemplary system in an open loop mode for controlling/ monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
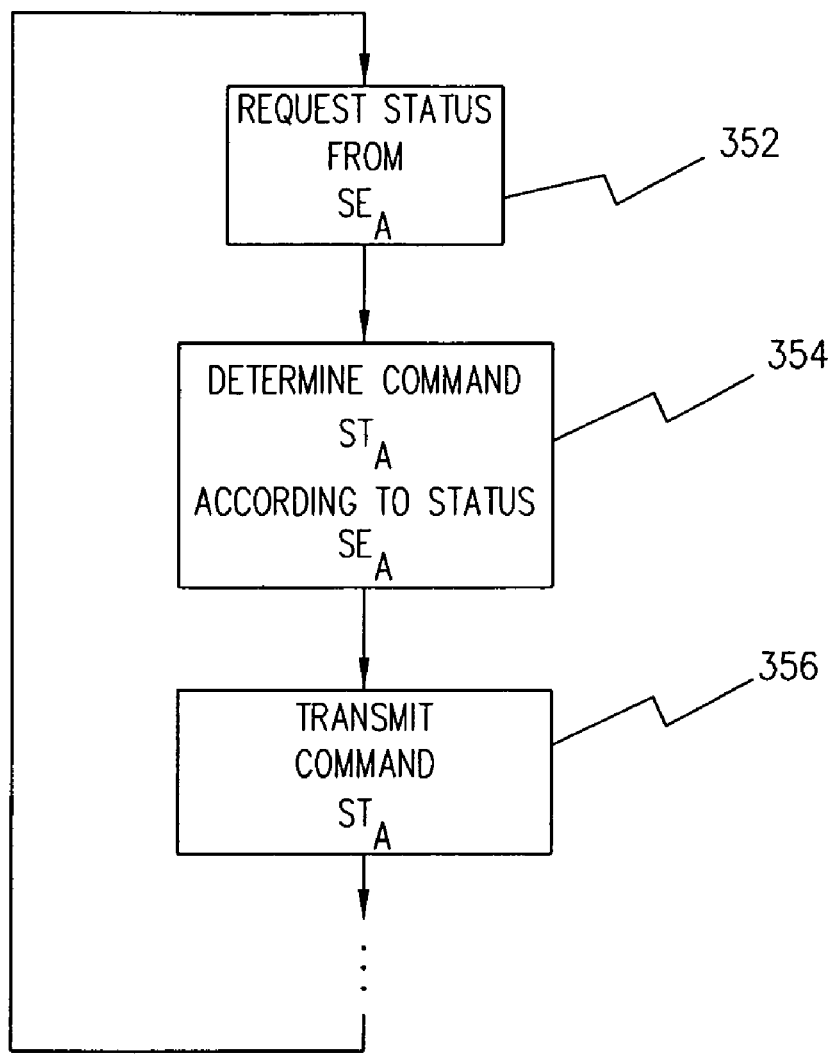
FIG. 5 shows a simplified flow chart of the use of closed loop control of a microstimulator by altering commands from the system control unit in response to status data received from a microsensor.

FIG. 5 is an exemplary block diagram showing the use of such a system to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (proportional, integral, derivative (PID)) control are preferably program controlled by the SCU 302 according to the control program contained in program storage 310.

Figure 6:
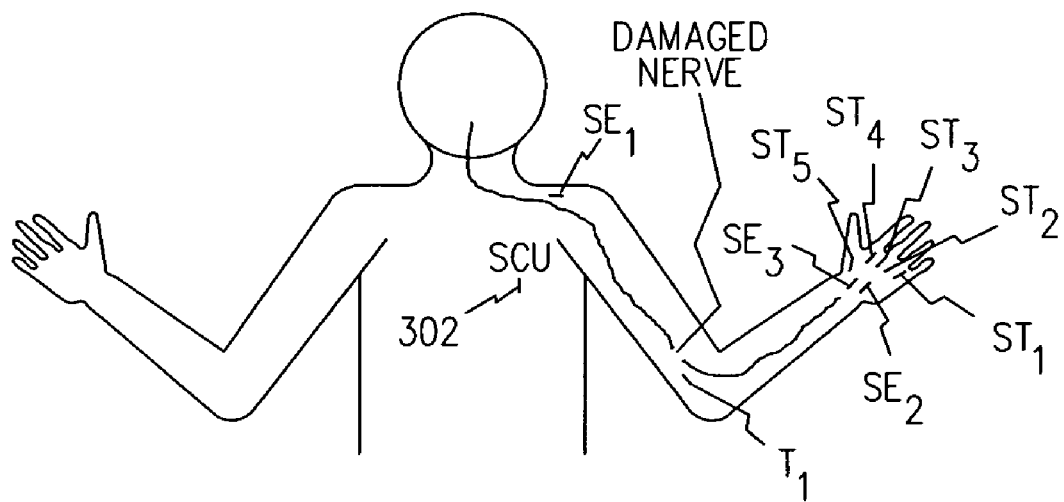
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by such a system 300. In this exemplary injury, the neural pathway has been damaged, e.g., severed, just above the patient's left elbow. The goal of this exemplary system is to bypass the damaged neural pathway to permit the patient to regain control of the left hand. An SCU 302 is implanted within the patient's torso to control a plurality of stimulators, $ST_1$-$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
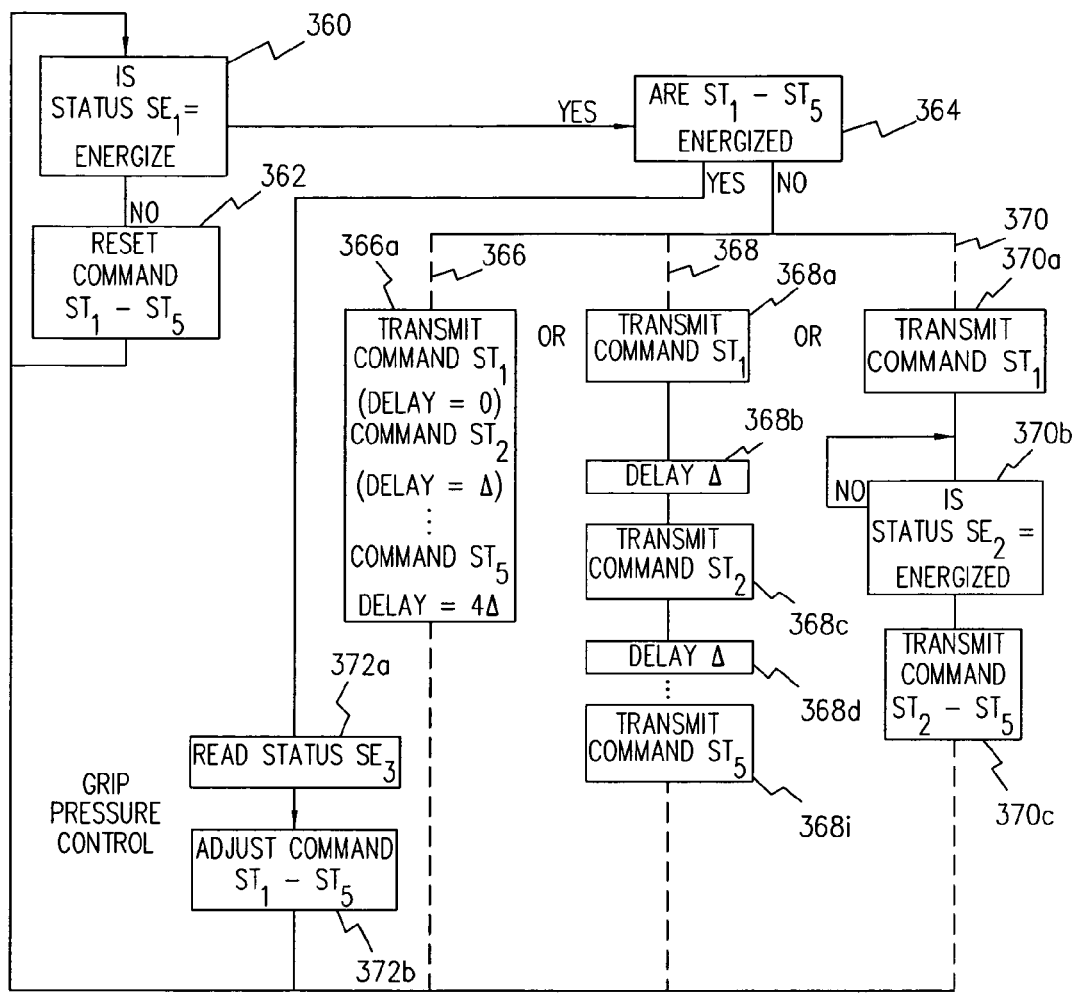
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$-$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$-$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor 2 ($SE_2$), before actuating the remaining stimulators ($ST_2$-$ST_5$) in block 370c. This implementation could provide more coordinated movement in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$-$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally positioned safety magnet 187 (see FIG. 1). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller circuitry 302 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume.

The battery 104 used for powering the implantable device 100 (or SCU 302) is made from appropriate materials so as to preferably provide a power capacity of at least 1 microwatt-hour. Preferably, such a battery, e.g., a Li—I battery, has an energy density of about 240 mw-Hr/cm$^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions).

A preferred system for practicing the present invention is comprised of an implanted SCU 302 and a plurality of implanted devices 100, each of which contains its own rechargeable battery 104. As such, a patient is essentially independent of any external apparatus between battery chargings (which generally occur no more often than once an hour and preferably no more often than once every 24 hours). However, for some treatment regimens, it may be adequate to use a power supply analogous to that described in U.S. Pat. No. 5,324,316 that only provides power while an external AC magnetic field is being provided, e.g., from charger 118. Additionally, it may be desired, e.g., from a cost or flexibility standpoint, to implement the SCU 302 as an external device, e.g., within a watch-shaped housing that can be attached to a patient's wrist in a similar manner to the patient control unit 174.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 to 10 watt-hours is preferred. While a primary battery is possible, it is preferable that a rechargeable battery be used. Such larger batteries will require a larger volume and accordingly, cannot be placed in the injectable housing described above.

Since only one SCU is required to implement a system, the battery life of the SCU may be accommodated by increasing the casing size (e.g., increasing at least one dimension to be in excess of 1 inch) for the SCU to accommodate a larger sized battery and either locating a larger SCU 302*a* (see FIG. 1) external to patient's body or a larger SCU 302*b* may be surgically implanted.

Figure 8:
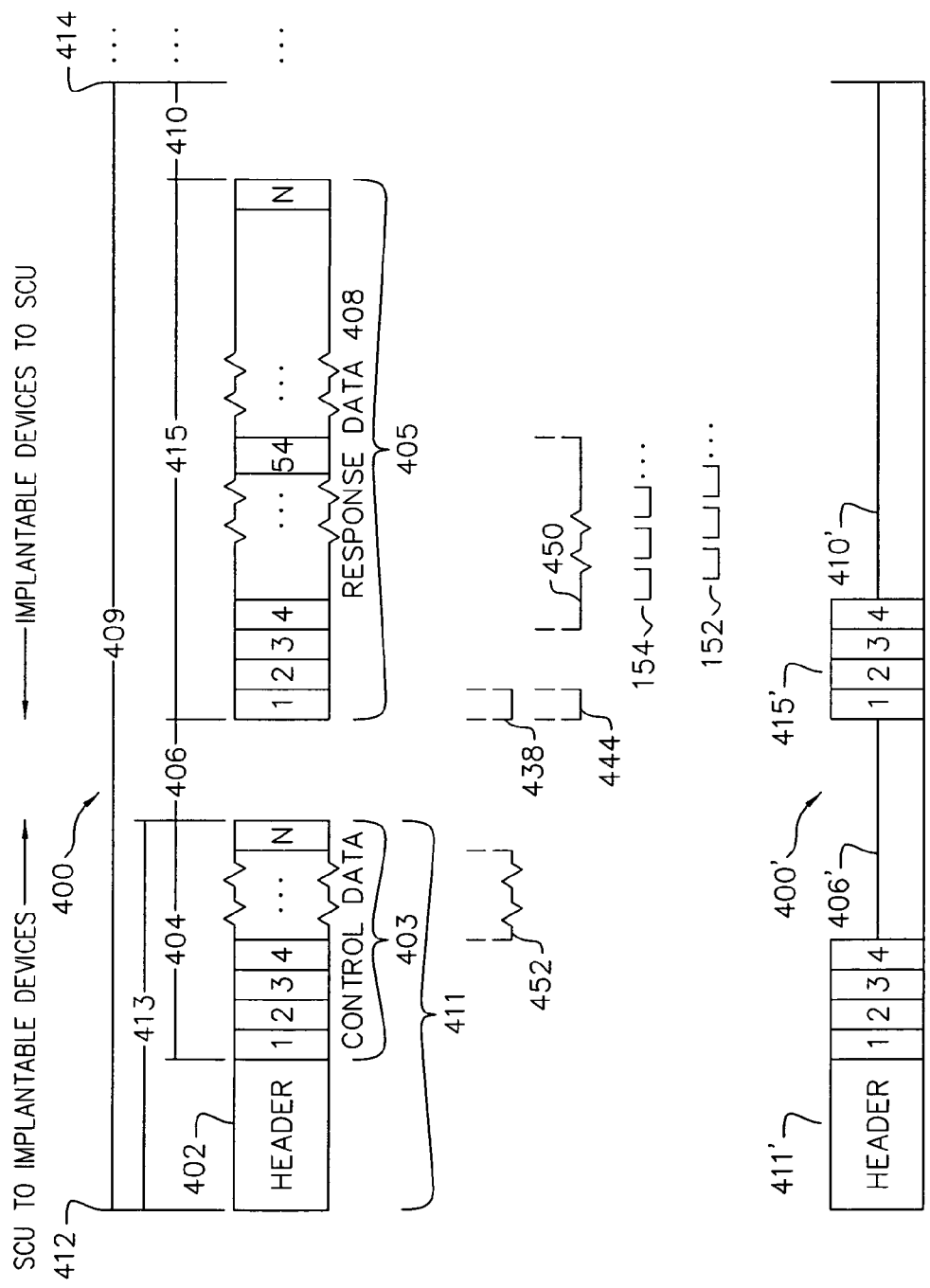
FIG. 8 is a simplified diagram of an exemplary communication protocol configured for master to slave communications in a partially populated system.

FIG. 8 shows a simplified diagram of a variant of the communication protocol described in commonly assigned U.S. Pat. No. 6,472,991 (herein referred to as the '991 patent) which is incorporated herein by reference in its entirety for communicating between the SCU 302 (see, e.g., FIG. 2) and a plurality of implantable devices 100.

For implementing the communication protocol, each implantable device 100, a slave device, uses the controller circuitry 106 which controls the operation of the implantable device 100 (as well as the implantable device's side of the communication protocol) and transfers data to and from the XMTR 168 and the RCVR 114*b* (which communicate with the SCU 302, a master device). The present communication system may accommodate a large number of implantable slave devices, e.g., preferably on the order of up to 1000 (or more) such devices, which preferably communicate with the SCU 302 in a half duplex manner, i.e., only one device may transmit data at a distinct time across a common communication channel (e.g., a single RF frequency that is shared using distinct time slots between multiple slave devices wherein the time slots are assigned to each slave device as part of an initialization sequence by the master SCU device 302 according to their unique ID code 303 during an initialization sequence). Data is typically directed from the SCU 302 to only one implantable slave device at a time.

The communication protocol is preferably configured to enable communication with N, typically greater than 256 devices, e.g., 1000 devices (or more). However, fewer devices may be used than allotted for in the communication protocol. For example, 10 devices may be used with a communication protocol that allocates time slots for 1000 devices. The communication protocol 400 of FIG. 8 is primarily comprised of (1) a header portion 402, (2) a control data portion 404 (including time slots 403), (3) a response delay portion 406 (which can approach 0), (4) a response data portion 408 (including time slots 405), and (5) a next frame period delay 410 (which can approach 0) resulting in a frame period 409 having a start 412 and an end 414 and a repetition rate of:

$$1/(\text{duration of frame period})$$

Collectively, the header portion 402 and control data portion 404 are referred to as the system control data message 411 that is transmitted during a system control time period 413. Similarly, the response data portion 408 occurs during a response time period 415. During the header portion 402, the SCU 302 transmits identification information that uniquely identifies the SCU 302. Additionally, as required in portions of the system control data message 411, assignment data is transmitted that assigns time slots to the implantable devices 100 (preferably as part of an initialization sequence that correlates the predefined ID 303 with a designated communication time slot or if an implantable device loses synchronization, the header can be used to resynchronize that specific device).

Preferably, the clock 312 in the SCU 302 (see FIG. 2) is a high precision crystal-controlled oscillator. However, since clock 312, used for controlling the operation of the implantable devices 100, is synchronized with data bit timing from the SCU 302 during each communication cycle, it does not need to be as precise. Accordingly, a lower precision and potentially lower power clock 312 may be used in the implantable device 100 and a retiming controller, e.g., a phase-locked loop, processes the output from the clock 312 and a received data stream from the RCVR 114*b* to generate a retimed clock during receipt of data from the SCU 302 by the implantable devices 100 (preferably during its time slot that was assigned according to its ID 303). See, for example, such an oscillator as described in copending commonly assigned U.S. patent application Ser. No. 10/280,841 entitled "Multi-Mode Crystal Oscillator System Selectively Configurable To Minimize Power Consumption Or Noise Generation" (herein referred to as the '841 patent application) as well as the disclosure and specifically FIG. 10 of the '991 patent, each of which is incorporated herein by reference. Preferably, the accuracy of the phase-locked loop is such that the retimed clock will maintain sufficient accuracy for multiple frame periods 409, e.g., 300 cycles.

Preferably, the data for each implantable device 100 is sent in order, e.g., from lowest time slot (403, 405) to highest time slot or vice versa. Thus, in FIG. 8, data is sent in time slot (403) 1 of the control data portion 404 to implantable device 1, in time slot (403) 2 to implantable device 2, etc. Similarly, data in the response data portion 408 is sent in the same order as that sent in the control data portion such that the time between time slot (403) 1 of the control data portion 404 and time slot (405) 1 of the response data portion 408 is that same as slot 2 of each data portion and the same as slot 3 of each data portion, etc.

Additionally, there may be a need for a system that has more implantable devices 100 than the aforementioned protocol would otherwise permit. For example, if the communication protocol allocates 1000 time slots, then 1001 or more implantable devices could not be directly supported. However, in a first alternative time slot sharing mode, the additional implantable devices may be supported by configuring one or more devices to alternately share a time slot.

To enable this alternative configuration, the SCU 302 preferably includes additional data in the header 402 and/or control data 404 portions to assign implantable devices to alternating portions of a time slot. For example, the SCU may instruct a first implantable device according to its address ID 303 to initialize its time slot to time slot (405) 1*a* and a second implantable device to time slot 1*b*. After this initialization, these two implantable devices would alternately share time slot 1, e.g., see for example time periods 438 and 444 which reflect time slots 1*a* and 1*b*, respectively, of the response data portion time slots 405.

Alternatively, there may be a need to increase the communication rate to one or more of the implantable devices 100. For example, suppose that a body parameter, e.g., a muscle depolarization signal, required more than the exemplary communication rate of 100 samples per second to be adequately measured or controlled, e.g., for fitting purposes. Additionally, suppose that this feature is only needed for a short time, e.g., during an analysis or fitting/calibration mode. While in the previously described first alternative mode, the battery life may be extended by decreasing its communication rate, a second alternative mode (implantable device to SCU streaming mode) may shorten the battery life to achieve this communication rate enhancement. However, should this operation be required during a fitting mode, an external charging magnetic field may be supplied to provide power to the implantable device 100. To enable this second alternative mode, the SCU 302 preferably includes additional data in the header 402 and/or control data 404 portions to assign implantable devices to multiple, preferably contiguous, time slot portions. For example, the SCU 302 may instruct a first implantable device according to its address ID 303 to initialize its time slot to time slots 4-54 (see extended time slot period 450) while temporarily disabling any other devices that may have previously been enabled in these time slots. Preferably, one or more implantable devices may be configured to operate in this second alternative mode. While this second alternative mode may be extended to enable a single implantable device to communicate during all of the available time slots, it is preferable to not fully implement this feature if there are implantable devices, e.g., heart pacing devices, that require periodic communications. In such cases, specified time slots, e.g., 1-3, are reserved for these required devices. Preferably, the extra allocated time slots are released under control of the SCU 302 when they are no longer needed and reassigned to other implantable devices.

Generally, communication from the XMTR 168 can occur concurrently with measurements or stimulation using the sensor circuitry 188 or stimulation circuitry 110 via the same set of electrodes 112*a*, 112*b* since the communication frequency used by the XMTR 168 is considerably higher than sensed or stimulated frequencies. (Alternatively, the sensor/stimulation circuitry may use a different set of electrodes 112*c*, 112*d*.) However, in some cases, it may be desirable to alternate sense/stimulate modes with transmit modes. Such an operation is shown as time periods 152 and 154, respectively. Alternatively, while the communication occurs during a portion of the response data portion 408, the associated sensed or stimulated data may be spread/buffered over the duration of the entire communication protocol, e.g., 402, 404, 406, 408, 410 and then communicated in a consolidated burst during one or more time slots during the response data portion 408.

In a third alternative mode (an SCU to implantable device streaming mode), the SCU 302 may, alternatively, allocate multiple time slots, e.g., 452, in the control data portion 404 of the system control data message 411 to a selected implantable device 100 and thus transmit more data in a frame period 409 to the selected implantable device 100. For example, such a high speed transmission of data, e.g., using 90% of the available communication time slots, could be used to send an audio data message by stimulating the patient's auditory nerve. The electrodes could also be hooked up to an implantable sonic transducer (speaker) which could reside in or near the middle ear or under the skin of the patient's middle ear. Messages such as "Low Battery", "Five Hours to Battery Depletion", "Move Arm Into Charging Field", etc. could be a useful way to communicate with the patient.

As has been described in reference to the '284 patent, it is apparent that systems of such devices (a master device and associated slave devices) can accomplish many useful functions. For example, the treatment of urinary incontinence is described in U.S. Patent Publication No. 2003/0018365, the treatment of erectile dysfunction is described in U.S. Patent Publication Nos. 2003/0236557, 2004/0015204, 2004/0015205 and U.S. Pat. No. 6,650,943, the treatment of sleep apnea is described in U.S. Patent Publication No. 2001/0010010 and U.S. Pat. Nos. 6,240,316 and 6,345,202, treatment and avoidance of atrophied muscles (e.g., following a stroke) is described above and in U.S. Patent Publication No. 2003/0093131, and U.S. Pat. No. 6,658,301, the treatment of disorders of gastrointestinal peristalsis is described in U.S. Patent Publication No. 2002/0123774, the treatment for control of bowel function is described in U.S. Patent Publication No. 2002/0072779 and U.S. Pat. No. 6,658,297, vagus nerve stimulation is described in U.S. Patent Publication No. 2003/0236558, control of a prosthetic or robotic device is described in U.S. Pat. No. 6,695,885, replacement of inoperative neural pathways (e.g., for treating paralysis) is described above, heart (cardiac) pacing is described above, etc. As such systems become more prevalent, it is possible that patients using such systems may encounter each other (see FIG. 9A) and should be allowed to coexist in proximity to each other. It should be apparent that it would be at least undesirable to have any one of such systems interfere with the operation of another one of such systems. While the presence of identification codes in each of the devices and their use in portions of the communication protocol should avoid any one master device controlling any slave devices in another such system (and likewise avoid any slave device from communicating with the wrong master device), the use of a common communication channel, e.g., a common RF frequency, may still allow devices in one system to interfere/block communications with devices in another such system. For example, while ongoing treatment of atrophied muscles in one patient might be desirable, it must not be allowed to interfere with a system used for cardiac pacing in another patient.

Fortunately, a typical system is not fully populated, i.e., the number of implantable devices 100 corresponding to the maximum number (N) of time slots allocated by the described communication protocol is not reached. Accordingly, FIG. 8 also shows the protocol 400' of a smaller exemplary system that has only 4 devices. Accordingly, time periods 413' and 415' are significantly shorter than time periods 413 and 415, respectively, while time periods 406' (the time between the system control time period 413 to the response time period 415, e.g., an extended response delay portion 406) and 410' (the time between the response time period 415 and the next system control time period 413, an extended next frame period delay 410) are significantly increased. Consequently, embodiments of the present invention can accommodate multiple systems being present in a common environment, e.g., if there are two patient's with implantable devices that are in close proximity, by interleaving the allocated portions 413', 415' of the communication protocols of each system that is within interference communication range of another such system (see FIG. 9B which shows an example of the interleaving of the frame periods 409-1, 409-2 and 409-3 of the three respective systems 300-1, 300-2 and 300-3 of FIG. 9A). To accomplish this, embodiments of the present invention temporally shift the frame periods 409 and consequently the unused portions 406', 410' of another such system that both use a common communication channel via use of this temporal displacement. This occurs by the selected (local or remote) master device, e.g., SCU 302, changing the start 412 of its frame period 409 and coordinating this change with its associated slave devices, e.g., implantable devices 100. As shown in the simplified example of FIG. 9C, the interference between two potentially interfering systems with frame periods 409-4 and 409-5 is removed by either shifting the start of the frame period of one system temporally to the right, as shown by arrow 409-5B pointing to the right, (i.e., delaying the start of subsequent frame periods by a portion of a frame period) or shifting the start of the frame period of the other system temporally to the left, as shown by arrow 409-4A pointing to the left, (i.e., advancing the start of subsequent frame periods by a portion of a frame period). This procedure may be extended to include multiple such systems; however, the temporal shifting is preferably done one system at a time. Preferably, the determination as to which system shall do the temporal shift is determined according to the unique ID 303 of the master device of each of the potentially involved systems, preferably deferring to systems having the higher value ID. Thus, the system having the lower ID value is preferably the one chosen to temporally shift its frame period 409, preferably to the right, i.e., delayed in time. Preferably, this temporal shift is done in such a way to prevent interference with any other known systems.

In embodiments of the present invention, one or more beacon messages are transmitted by each master device, e.g., SCU 302, each frame period 409 for reception by other master devices. The beacon messages are integrated into a relatively small portion of an adaptation (described further below in reference to FIG. 10) of the aforedescribed communication protocol. Preferably, at least one of these beacon messages is at a fixed location during the frame period and at least one other beacon message is at a random, e.g., semi-random, location selected from a predefined set of locations in the frame period. At least some of these beacon messages include (1) the ID 303 of the transmitting master device and (2) the quantity of communication time slots allocated to its one or more associated implantable devices (while this typically corresponds to the number of implantable devices, this may be a different value when any of the aforedescribed special communication modes are employed in which communication time slots may either be shared by multiple devices or a single device may share multiple communication time slots). Upon receipt of a beacon message from another master device, priority is preferably determined according to the relative magnitudes of the received ID of a remote master device to that of the ID of the receiving local master device. Typically, the lower priority device (preferably the master device having a lower numerical value for its ID) is selected to offset its frame start location to eliminate any potential interference with the other master device or other master devices that it is currently aware of (other variations are discussed further below). Note that the terms local and remote are relative. In each system, its master device is a local master device as compared to the master devices of all other systems which are remote master devices. Thus, in FIG. 9A, relative to 302-1, 302-1 is a local master device and 302-2 and 302-3 are remote master devices. However, relative to 302-2, 302-2 is the local master device and 302-1 and 302-3 are remote master devices.

It should be apparent that use of solely a fixed beacon, i.e., a beacon having a fixed offset from the start of the frame period, will generally not suffice (unless each local master device periodically ceases transmissions to allow other master device communications to occur without interference from at least the local master device) since, as shown in FIG. 9C, a fixed beacon, e.g., in the system control time period 413-5, of one system might overlap and thus interfere with receipt of a similar fixed beacon from another device. This applies to any position of a fixed beacon and accordingly wandering beacons are preferably used to increase the probability that beacons will not overlap. As such, the location of the wandering beacon preferably changes each frame period, e.g., as selected at least in part with a random number generator, to further decrease the probability that the wandering beacons could overlap and interfere. As described further below, the locations of wandering beacon messages of the present invention are preferably selected from a predefined set of frame period offset values such that the relative offsets of any two wandering beacon messages can be used to calculate the actual start of the frame period of a remote system. As described further below, beacon messages have two parts: 1) a beacon marker code, and 2) a data portion. Preferably, the beacon marker code is a 31 baud long string of QPSK symbols. Alternatively, the beacon is a 63 baud long string of BPSK symbols. Preferably, there are 4 such strings, each unique from each other and unique from other transmitted data. It is currently estimated that these strings will have a processing gain of +18 dB based upon a single reception without any integration. Next, after the beacon marker code comes the data portion. The data portion is comprised of several words. Preferably, each word is comprised of 32 bits transmitted as 16 QPSK symbols with 5 bits encoded to make these 32 bits or 32 possible unique codes. Because the data portion follows closely behind the beacon message code, the beacon message code establishes a phase reference for the message that follows. If the data portion is phase corrected based on the phase of the beacon message code, several such data portions can be added up. In a preferred embodiment, eight successive data portions are added to get an integration processing gain, currently estimated to be about +9 dB. By adding the integration processing gain and a 5 to 32 coding gain, a +18 dB processing gain (current estimate) is achieved for the data portion.

In embodiments of the present system, the local master device has the ability to detect the presence of beacon messages, e.g., fixed or wandering, from a remote master device at a communication range, e.g., a beacon detection communication range, while the systems are still outside of an interference communication range. The aforementioned processing gains allow recognition and extraction of beacon messages and their data in advance of any actual inter-system interference to other, typically varying, communications that are less heavily coded and not as susceptible to detection via integration. Thus, if the systems are still too far apart to have beacon messages received from another system, then the other system will not actually cause interference.

Once it is determined which system is to relocate the start of its frame period, the selected master device communicates with each of its one or more associated slave devices and causes each of the devices of the selected system to move its temporal position, preferably essentially concurrently, with no control communication loss (or no more than a few frame periods associated with the frame relocation). Once the start of the frame period of the selected system is relocated, interference will be avoided even if the systems come close enough to have otherwise caused actual interference since the data message portions of each system will now be interleaved. This process may be repeated, preferably one system at a time, when multiple systems are within a beacon message receipt range of each other.

Figure 10:
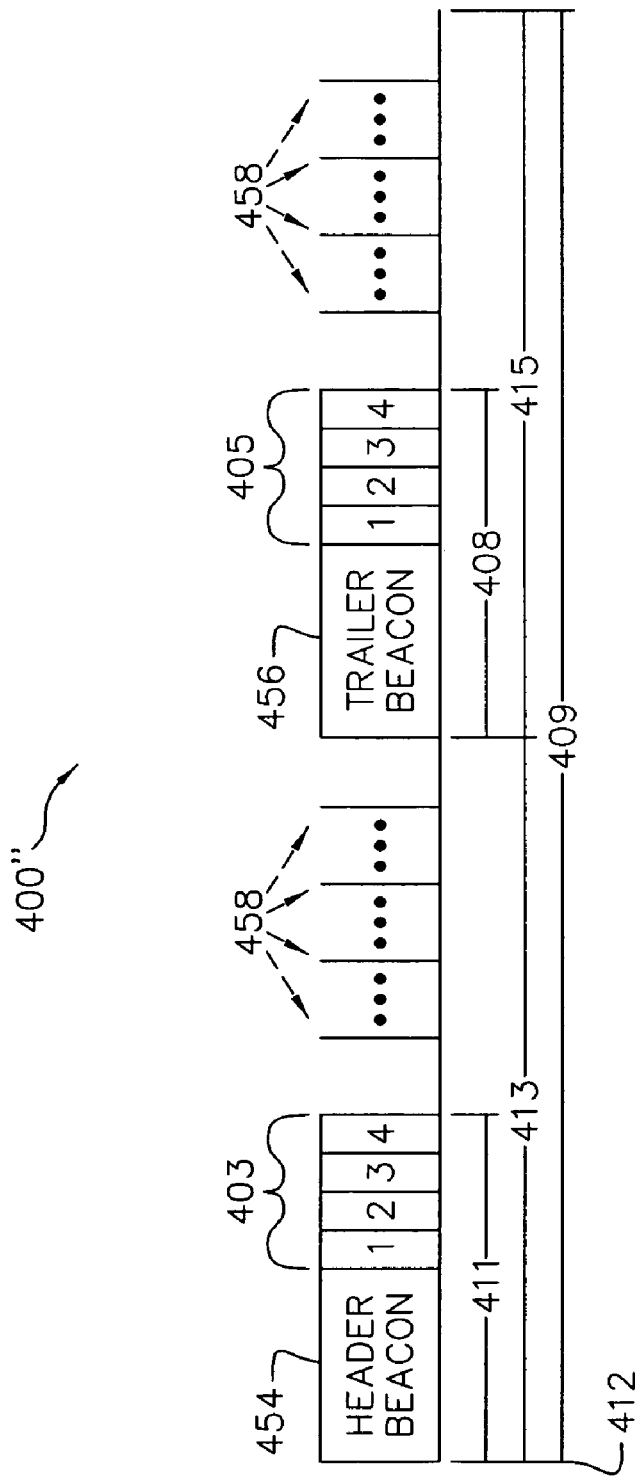
FIG. 10 is a simplified diagram of an exemplary communication protocol configured for communications between a master and one or more slaves that is suitable for use in embodiments of the present invention to enable multiple such communication systems to coexist in close proximity.

The beacon messages may exist in various locations throughout the frame period (see FIG. 10 for the modified communication protocol 400" of the present invention). Specifically, a header beacon message 454 (see FIG. 17 having a first heavily-coded marker code portion 460 and a data portion 462) will preferably be included as the first portion of the system control time period 413 while a trailer beacon message 456 (see FIG. 18 having a second heavily-coded marker code portion 464 and a data portion 466) will preferably begin the response time period 415. Wandering beacon messages 458 (see FIG. 19 having a third (and preferably a fourth, as described further below) heavily-coded marker code portion 468 and a data portion 470) may exist in any available location (selected from a predetermined set of locations) throughout the frame period 409. In an exemplary system, 864 time slots are available for sending data to and preferably an equal number of time slots for receiving data from the one or more associated slave devices of which 864 slots are available for allocation to individual slave devices. Accordingly, a total frame period 409 consists of 1728 usable time slots of which half of which are in a downlink portion (master to slave communications in time period 413) and the other half of which are in an uplink portion (slave to master communications in time period 415). Table I shows a predefined set of 16 potential slots for placing these wandering beacon messages. What is notable is that these locations are selected such that relative temporal differences between any two such beacon messages are unique and can be used to identify the frame start location 412 of a remote master device and its associated slave devices.

TABLE I

Wandering Beacon Message Transmission Starting Locations

| Location index | Starting slot | End slot | Uplink/Downlink |
| --- | --- | --- | --- |
| 1 | 1717 | 1727 | Uplink |
| 2 | 1620 | 1630 | Uplink |
| 3 | 1522 | 1532 | Uplink |
| 4 | 1423 | 1433 | Uplink |
| 5 | 1323 | 1333 | Uplink |
| 6 | 1222 | 1232 | Uplink |
| 7 | 1120 | 1130 | Uplink |
| 8 | 1017 | 1027 | Uplink |
| 9 | 913 | 923 | Uplink |
| 10 | 808 | 818 | Downlink |
| 11 | 702 | 712 | Downlink |
| 12 | 595 | 605 | Downlink |
| 13 | 487 | 497 | Downlink |
| 14 | 378 | 388 | Downlink |
| 15 | 268 | 278 | Downlink |
| 16 | 157 | 167 | Downlink |

FIGS. 11-13 show additional tables generated from processing the values found in Table I. While each of these displacement tables can be generated "on the fly" it may be desirable that usable portions of these tables be generated as part of an initialization sequence or originally stored in a table to minimize real time processing requirements. For the purposes of this patent application, this data, whether physically residing within a table or generated "on the fly", is referred to as a displacement table. FIG. 11 shows a 16×16 matrix of the potential temporal differences between two different wandering beacons. Each of these differences is unique and can identify the frame start location. FIGS. 12-1 through 12-3 shows a 120×2 table (240 entries) that enumerates the correspondence between the temporal displacements of two wandering beacon messages and a temporal offset from the frame period of a local master device to determine the start of the frame period of a remote master device. Alternatively, FIG. 12 shows a lookup table having 1560 entries (most of which are inapplicable as noted by "-------") that may be used to identify the frame period offset. For example, if a beacon offset of 378 (beacon 14) was received in one frame period and a beacon offset of 268 (beacon 15) was received in another frame period, an absolute value (i.e., the order of receipt of the beacon messages is irrelevant) difference of 110 time slots would be determined according to the master device's clock 312. Now, referring to the table index of 110 into the table of FIG. 13, a value of 268 is found. This value signifies that the start of the remote master device's frame period is 268 time slots before the earliest received beacon, i.e., beacon 15 in this case. By referencing the relative time receipt of the earliest received beacon, i.e., beacon 15, as compared to the local master device's frame period, the relative start of the frame period of the remote master device may be determined. This data is then stored in a local database along with the number of allocated time slots. This data is used for the selected lower priority device in determining the needed frame period offset to avoid interference. Additionally, it should be noted that the inapplicable data values (noted here as "------") actually reference useful data. When only a single remote master device exists, the determined difference values should correspond to specified values in the lookup table of FIG. 13. However, if there are multiple remote master devices, two detected wandering beacon messages will not always match one of the specified values. If an inapplicable code is fetched from the table, it may indicate that beacon messages were received from two different master devices. The heavily-coded marker code portion of the beacon message facilitates identification of the beacon message in a single frame. However, embodiments of the present invention, preferably integrate the remaining data portions of the beacon message over multiple, e.g., 8, frame periods to facilitate extraction of the data portion from a relatively low S/N signal. By noting which beacon messages can correspond to each other, i.e., when pairs of identified beacon messages fetch valid data from the table of FIG. 13, it is determined which data portions should be integrated, e.g., summed or accumulated, and which portions should be integrated with other identified beacon messages. It should be noted that while the simplest confrontation is between a pair of systems (see FIG. 9C), this may not always be the case. Accordingly, if three (see FIG. 9B) or more systems are in sufficiently close proximity, it is preferable that the beacon messages periodically, e.g., every 8 frame periods, change to allow communications to be specifically directed to another system. Preferably, when this occurs, the heavily-coded marker code portion 468 of the wandering beacon message 458 changes from a third to a fourth unique marker code to facilitate identification of this transition.

Figure 14:
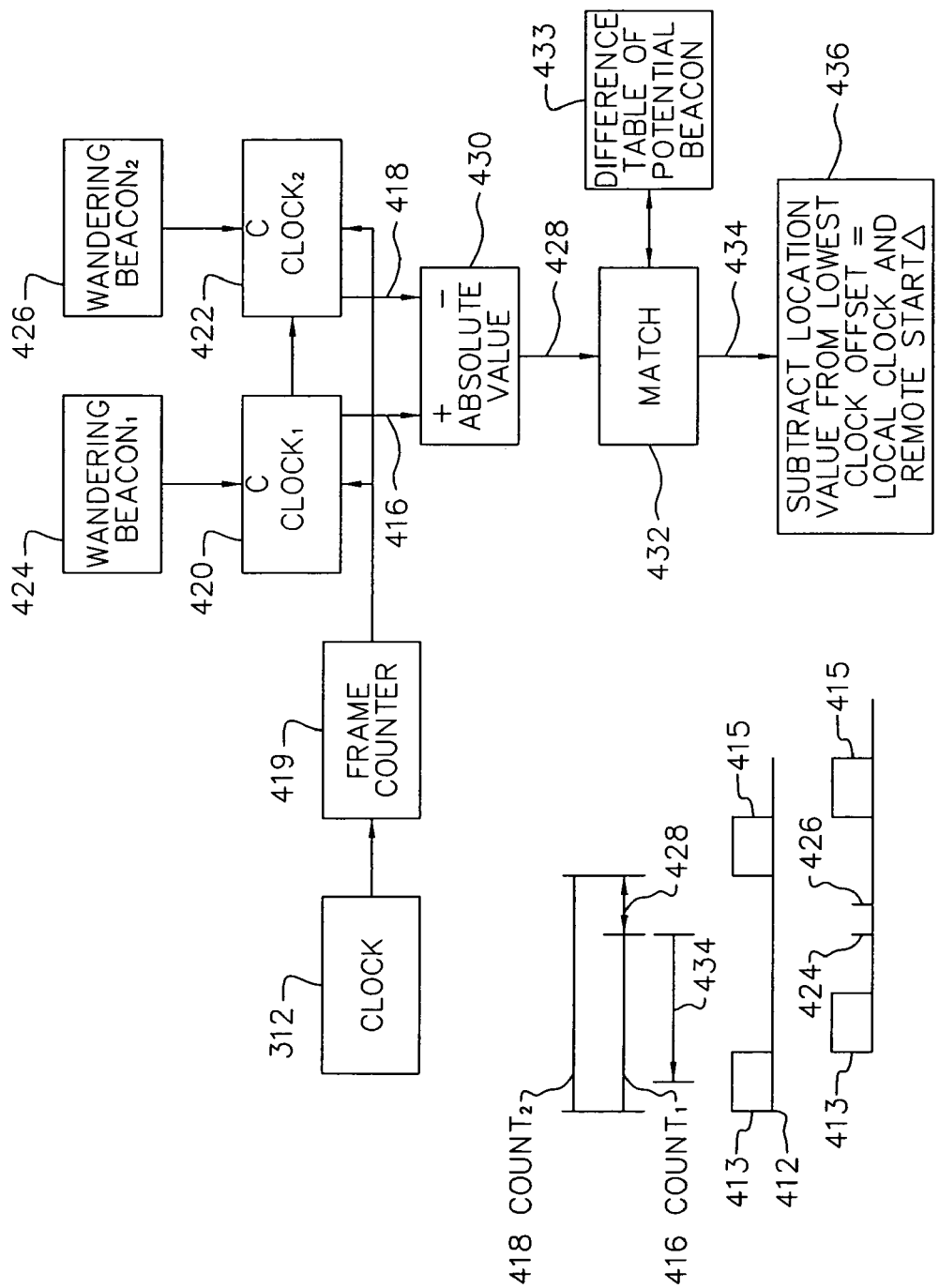
FIG. 14 shows an exemplary flowchart of a technique for using one or more of the tables of FIGS. 11-13 to process two wandering beacons to determine the start of the frame period of a remote master device.

FIG. 14 shows an exemplary flowchart of a technique for using one or more of the tables of FIGS. 11-13 to process two wandering beacon messages according to the aforedescribed algorithm. In two different and preferably (but not necessarily) temporally contiguous, i.e., consecutive, frame periods 409, frame counter values 416 and 418 derived from frame counter 419 driven by clock 312 are clocked into latches 420 and 422 when wandering beacon message₁ 424 and wandering beacon message₂ 426 are received. The absolute value 428 of the latched values is then determined in block 430 and a match, lookup, processed calculation or the like is performed on difference table values 433, e.g., the tables of Table I, FIGS. 11-13, etc. or the like, and this processed value is then used in block 432 to determine the offset 434 from the start of the local frame counter 419 and thus determine the start of the frame period of a remote master device in block 436. As noted above, if there are multiple remote master devices, two detected wandering beacon messages will not always match one of the specified values. If an inapplicable code ("------") is fetched from the table, it may indicate that beacon messages were received from two different master devices. Alternatively, it may mean that the two beacon marker codes originated from two or more different masters or it may mean that the remote master has performed a temporal shift between the time that the first and second beacon marker codes were received. The heavily-coded marker code portion 468 of the beacon message 458 facilitates identification of the beacon message in a single frame. However, embodiments of the present invention, preferably integrate the remaining data portions 470 of the beacon message 458 over multiple frame periods to facilitate extraction of the data portion 470 from a relatively low S/N signal. By noting which beacon messages can correspond to each other, i.e., when pairs of identified beacon messages fetch valid data from the table of FIG. 13, it is determined which data portions should be integrated, e.g., summed or accumulated, and which portions should be integrated with other identified beacon messages.

Figure 15:
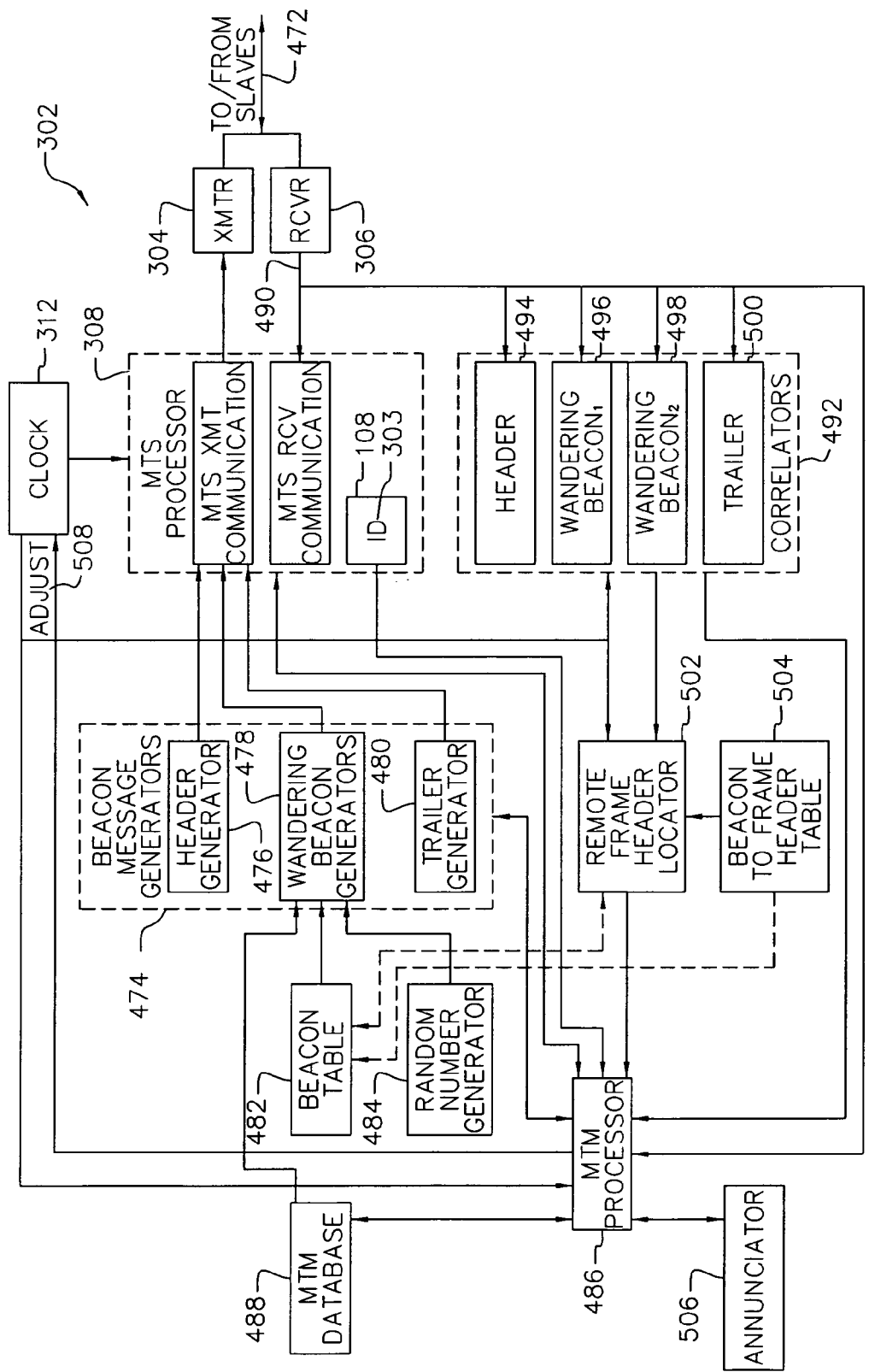
FIG. 15 shows a simplified block diagram primarily showing the additional structure added to that already shown in FIG. 2 for generating and processing the beacon message portions of the present invention that are used to interleave communications between multiple systems of devices on a common communication channel.

FIG. 15 shows a simplified block diagram primarily showing the additional structure added to that already shown in FIG. 2 for generating and processing the beacon message portions of the present invention that are used to interleave communications between multiple systems of devices on a common communication channel. Essentially, this additional structure adds on to the previously described SCU 302 (herein referred to more generally as a master device) comprised of a programmable controller 308 (herein referred to more generally as a master to slave (MTS) processor) and a signal transmitter 304 for transmitting data to and a signal receiver 306 for receiving data from associated remote devices (herein referred to more generally as slave devices), e.g., implantable devices 100 across a common communication channel 472, e.g., a common RF channel. It is understood that additional functionality exists in the MTS processor 308 for actually processing the transmitted and received data communicated with the remote slave devices as has been described above (but not expressly shown in this simplified block diagram). These communications occur according to a high precision clock 312 (see for example the crystal oscillator of the aforementioned '841 patent application) and are controlled in part according to the ID 303 stored in address storage circuitry 108 according to a subset of the communication protocol described in the '991 patent as further described above. Embedded within the communications protocol 400' (see FIG. 10) are the aforementioned header 454, wandering beacon 458, and trailer 456 messages as generated by the beacon message generators 474, i.e., a header generator 476, wandering beacon generators 478, and a trailer generator 480. The wandering beacon messages 458 are determined according to beacon table 482 which defines a set of predefined offsets from the start 412 of a frame period 409, e.g., see Table I which shows a set of 16 such offsets. Preferably, a random, e.g., semi-random, number generator 484 or the like is used in part to select a different available entry from the beacon table 482 (e.g., selected from entries that do not conflict with locations for known local or remote devices) for each frame period 409 until all entries have been used. Preferably, no available value will be used twice before all potential values have been used. Additionally, the potential locations for the wandering beacon messages 458 are further limited by the number of time slots (generally corresponding to the number of slave devices) used in the communication protocol 400" of each system and the known locations and slots used in each detected remote system to avoid interference with the known remote systems. These calculations are done by a master to master (MTM) processor 486 and accumulated in a master to master (MTM) database 488. Preferably, there are multiple wandering beacon generators 478 or a single one capable of generating wandering beacon messages 458 with different marker codes 468. This is to accommodate situations where three or more master devices are within physical proximity to each other which may cause communication interference and this feature allows each master device to facilitate inter-system communications by transmitting messages for a plurality, e.g., 8, of frame periods with specialized data acknowledging the presence of one remote master device and then shifting to another type of wandering beacon message 458 for a next remote system.

Signal receiver 306 provides a data stream 490 to a set of correlators 492, e.g., one for each of the beacon message types, e.g., header, wandering beacon₁, wandering beacon₂, and trailer, where these correlators 494, 496, 498, 500 are configured to detect the heavily-coded marker codes for their respective beacon message types and a remote frame header locator 502 in coordination with a beacon to frame header table 504 may integrate, e.g., accumulate, the data portions of the respective beacon messages, over multiple, e.g., 8, frame periods 409 to extract the data contained within. As previously discussed, the heavily-coded marker code portions can be processed to achieve a high processing gain, e.g., currently estimated at approximately +18 dB, and a similar high processing gain, e.g., currently estimated at approximately +9 dB, can be achieved by the integration of the data portion 470 (which need not be as heavily coded). As previously discussed, multiple remote master devices may exist. Accordingly, the beacon to frame header table 504 using a data format similar or equivalent to that shown in FIG. 13 or derived from the beacon table 482 (see, for example, FIGS. 11 and 12-1 through 12-3) may determine which data portions correspond to the same remote system and thus determine which data portions to integrate, e.g., in distinct data bins, and thus achieve the desired data processing gain. Once the remote frame header locator 502 has determined the start location 412 of a remote frame period, this data is processed along with the associated number of time slots used which is contained within data portions of the beacon messages and this data is stored within the MTM database 488. Preferably, the retention of data within this database is time limited, i.e., if a remote system is not detected for a predetermined period of time, data corresponding to this remote system is purged from the MTM database 488 since this remote system is effectively no longer an interference threat. However, once a remote system has been detected and it is determined that interference between the remote and local systems may occur (due to the present relative temporal positions of their frame periods and their use of time slots within their frame periods), the MTM processor 486 determines according to its local ID 303 and the ID found in the beacon messages of the remote master devices, which system, e.g., the system having the lowest numerical value for its ID, should adjust its start location. Preferably, the remote master device that recognizes that it has the lowest priority alters its beacon messages, e.g., using its wandering 478 and trailer 480 generators, to add an acknowledge (ACK) code 467 to notify the other master devices that it will be performing the move. Preferably, the ACK code 467 is redundantly present in the trailer beacon message 456 to allow its ACK data to be integrated within a single frame period, i.e., the multiple ACK codes 467 are summed from a single trailer beacon message 456 (see FIG. 18) to achieve a desired processing gain. Once a system has acknowledged that it is going to move its frame period, the MTM processor 486 communicates with its one or more associated slave devices and completes this move, e.g., by delaying the start of its frame period, within one frame period (or a limited number of frame periods). This process preferably repeats until all potential interferences are eliminated.

However, it is possible that the master device that should move, e.g., the master device having the lowest numerical value for its ID, does not acknowledge that it will be making the move. Accordingly, a higher priority master device will preferably move its start location after a predetermined timeout where an ACK code is not received from the lower priority device. Preferably, in this case, the start 412 of the frame period 409 will be advanced (or delayed by a period of time less than a frame period). Accordingly, should the inter-system communications partially fail, both systems may move in opposite directions and thus, potentially, move a further temporal distance from each other.

However, depending upon the complexity, i.e., the number of devices in each of the systems and the number of systems present, the aforementioned solutions may not directly resolve the potential interference. Accordingly, embodiments of the present invention optionally include additional alternative responses. In a first alternative response, it may be noted that, due to the departure of one of the previously present interleaved systems, there may be non-contiguous temporal gaps. Should these gaps be combined into a single contiguous gap, there may then be a sufficiently large gap to permit another interleaved system to coexist. Accordingly, when such a situation occurs, one or more of the systems may be instructed by the highest priority master device (or determined automatically by the local master device) to reposition their frame periods. In a second alternative response, one or more of the systems may be instructed to have one or more of its slave devices share time slots and thus effectively increase the potential temporal bandwidth. In a third alternative response, all of the systems can be instructed by the highest priority master device to increase the duration of their frame periods 409. In such a case, critical devices may also be instructed by their respective master devices to use multiple time slots and thus increase their effective repetition rates. Each of these solutions allow more systems to share a common communication channel. In a fourth alternative response, one or more of the systems could be instructed by the highest priority master device (or determined automatically by their local master device) to move to a different communication channel, e.g., a different RF frequency. Finally, there may be no solution available. In such a case, it is preferable that an annunciator 506 be available to alert the patient that they are moving too close to one or more systems that may interfere with their system. While a discrete, e.g., physical, annunciator, e.g., a beeper, is shown, systems of the present invention may instead instruct a slave device to provide a warning response to a user. For example, a slave device that functions as a muscle stimulator could provide a recognizable twitch or otherwise provide a physiological notification to alert the user before a more adverse response could occur from inter-system interference.

Once the frame periods have been successfully interleaved, it is still possible that interference will periodically occur due to differences between the clock frequencies and clock drift of different systems. There are multiple solutions to this potential problem that are each considered to be within the scope of the present invention. In a first case, it is considered to be likely that there will be some clock frequency differences and that occupied time slots of multiple systems will eventually drift toward or away from each other. When master devices note that the systems approach interfering with each other, e.g., by monitoring for a minimum temporal gap between the occupied time slots of each system, the lower priority master device can recognize this situation and automatically (or in response to additional information from another master device) reposition its frame period. This solution offers some advantages. First, this solution is essentially inherent in implementations of the aforedescribed protocol. Second, when one or more systems leave the proximity of other interleaved systems, one or more potentially non-contiguous gaps may remain. If these gaps are forced into being contiguous, e.g., by allowing this drift to cause one or more of the frame periods to be eventually repositioned, a larger gap would result and thus increase the probability that a sufficient gap would then exist for the next potentially interfering system to coexist over the common communication channel.

In a next solution, the clocks 312 of each of the systems are synchronized, e.g., to the clock of the master device having the highest priority. The error between clocks 312 can be determined by monitoring the differences between the temporal position, e.g., phase or the like, of the beacon messages received from other remote master devices and causing the lower priority master devices to adjust the frequency and/or phase of its clock accordingly, e.g., using the adjust signal 508 (see the aforementioned '841 patent application which describes circuitry that is equally applicable to such a master device).

While discrete blocks have been shown, it is recognized that there are numerous equivalent ways to implement the described functions as would be recognized by one of ordinary skill of the art. For example, while an MTS processor 308 and an MTM processor 486 are individually shown, they could each be tasks within a common processor/controller, one or more of them could be implemented as portions of an ASIC or FPGA, etc. Additionally, while it is presently preferred that the correlators 492 be implemented as one or more ASICs or FPGAs, increases in available speeds of processors, e.g., DSPs, could alter that preference. Finally, while a discrete beacon to frame header table 504 is shown, it is recognized that this data results from processing data corresponding to the beacon table 482. Accordingly, the beacon to frame header table 504 may be generated as part of an initialization routine or might be periodically generated as needed.

Figure 16:
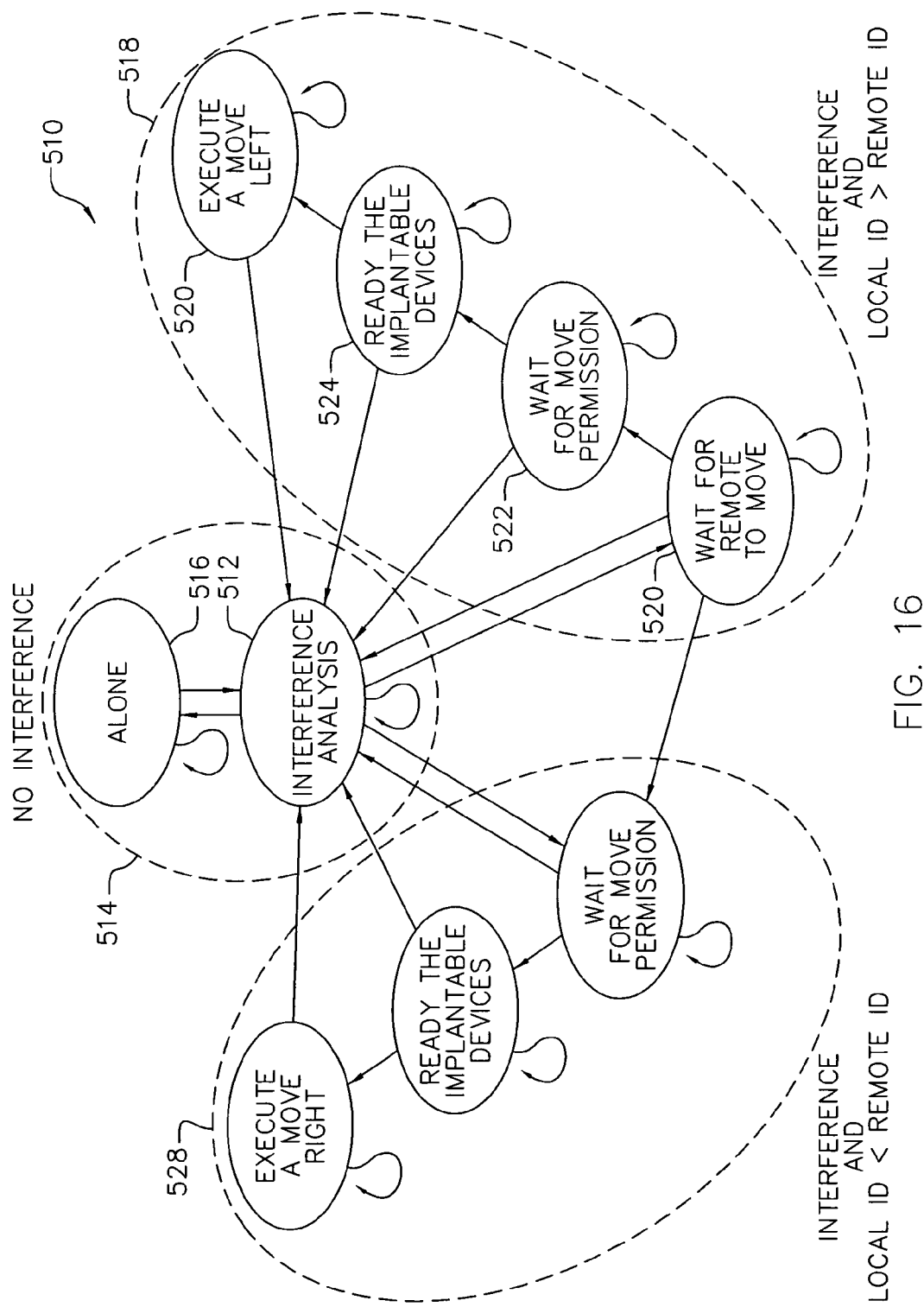
FIG. 16 shows a simplified block diagram for determining which master device will temporally move its frame period and the associated steps in moving its associated slave devices.

FIG. 16 shows a simplified block diagram of the process 510 primarily performed under control of the MTM processor 486 for determining which master device 302 will temporally move its frame period 409 and the associated steps in moving its associated slave devices 100. As previously described, the MTM processor 486 accumulates data in the MTM database 488 (see, for example, FIG. 20) in conjunction with the correlators 492 and the remote frame header locator 502. Using this accumulated data an interference analysis is performed in block 512, essentially by comparing the occupied time slots of each of the detected remote master devices (and associated slave devices) and the known occupied time slots by the local master device. If it is determined that there is no overlap (and preferably a sufficient time gap between the occupied portions of the frame periods), then it is determined that (1) there is either no interference (block 514) or (2) if the MTM database 488 does not presently have or no longer has data (since prior entries have been purged due to a programmed timeout that has elapsed since a remote master device has been detected), then the local master device is determined to be alone (block 516). In either case, no further action is currently needed by the local master device. However, if the local master device determines that there is interference (or an insufficient gap between the detected systems such that interference is likely to be imminent, the MTM processor 486 will determine which master device should instigate a temporal shift to allow the occupied time slots of the detected systems to be interleaved and thus avoid actual interference should the systems come in closer proximity. First, it must be determined which system has the lowest priority. Preferably, this is done accordingly to unique preprogrammed ID values 303 of each of the master devices. Additionally, it is preferable that multiple, e.g., 2, high order bits are assigned to preemptively give higher priority to systems that are crucial. For example, as previously discussed, a cardiac pacing system should have higher priority than a system that treats atrophied muscles. There is a 50/50 chance that the preprogrammed LSBs of the IDs 303 of each of these systems might allow an undesirable result since the master devices would typically be given their unique IDs 303 as part of the manufacturing process before they are actually assigned to a particular system. However, if a medical practitioner, is then given a subsequent opportunity to modify the MSBs of the ID code 303, this will remedy this potential conflict.

In a first case (block 518), the local master device determines that it has a higher priority than the remote master device. Accordingly, it is the responsibility of the remote master device to temporally shift its frame period 409 to allow it to interleave with the other systems that it has detected. Ideally, the remote master device having the lowest priority will reflect this responsibility by modifying the ACK codes 467 within its wandering 458 and trailer 456 beacon messages to alert the other master devices that it will be assuming its responsibility and making the temporal shift. Preferably, the ACK includes at least a portion of the ID values of the master devices. The remote master devices will receive these ACK codes 467 and await for the remote master device in block 520 to coordinate the move with its local slave devices in blocks 522 and 524 and then to make its temporal move in block 526. This information is then communicated back to the local master devices that notes via detected beacon messages that the start 412 of the frame period 409 of the lower priority remote master device has now shifted. Should this remedy the potential interference, the system now returns to the no interference state 514 where it continuously monitors for the next potential conflict. Additionally, the databases in the local and remote systems are updated to reflect the move. In certain situations there may be multiple potential conflicts because of multiple, i.e., three or more, systems being in close proximity. In such situations, this process may repeat for each lower priority system.

Conversely, as reflected in block 528, the local master device may determine that it is the master device of the system that should be making the temporal move. As noted above, the local master device will then alert the other remote master devices, via ACK codes 467 in its wandering 458 and trailer 456 beacon messages, that it will be making the temporal move. Generally, the procedure is the same as has been described above.

Finally, the case may exist when the lower priority master device either (1) does not sufficiently detect the other master devices to determine that it should be making the move or (2) the higher priority master devices fail to sufficiently detect the lower priority master device to confirm that the lower priority master device has confirmed its responsibility to make the move. Either of these cases could result in unpredictable or undesirable results. Accordingly, in embodiments of the present invention, a timeout counter is maintained, e.g., in the MTM database 488 to determine if a master device has failed to receive an acknowledgement (ACK code 467) within a sufficient time period. In such a case, the higher priority master device will perform a similar, but preferably in the opposite direction, temporal shift to remedy the potential interference. These moves are done in opposite directions to ensure that the potential interference is avoided, i.e., if they both moved in the same direction, the potential interference would still remain in a new temporal position. Should the systems come in closer proximity, the ability of the systems to detect each other (in advance of any actual interference) will increase and the likelihood of the necessity of this fallback case will be minimized.

In the above description, the communications between a master device and its one or more associated slave devices have described the use of embedded identification codes in each device to determine the group of devices assigned to each system and the time slot positioning within the frame periods of each such system for the slave devices. Additionally, the use of an embedded identification code in the master device has been described as providing additional information in determining the origin of beacon messages and, accordingly, the relative temporal position of the frame periods of other systems as determined by its remote master device. Also, the use of the identification code, has been described for determining the priority between two systems when potential (or actual) interference can occur. However, system embodiments can be envisioned in which an identification code is not required for the master to master communications. For example, when a master device sends out a wandering beacon, it can be sent out either earlier in the frame period or later in the frame period than the temporal position for the wandering beacon used in the prior frame period. Instead of using an identification code, each system tracks the pattern of earlier and later wandering beacons of the other system(s) and comparing that pattern to its own pattern of changing the temporal positions of its wandering beacon messages. The system that has its wandering beacon position shifted to an earlier position when the remote system has its wandering beacon message shift to a later position, is determined to be the system of lower (or higher as a design choice) priority, and thus the system that should reposition its frame period. As far as acknowledging another system, this may be done by a system transmitting the relative offset of the acknowledged system rather than its identification code as has been previously described. Additionally, since in this embodiment, there is no way to know when the remote system started counting early and late, each system would preferably indicate when it started counting the other system's pattern or "seed" for its own random number generators so that the other system can predict what this system is likely to do.

Exemplary Embodiment

A) Objective

The following describes an exemplary implementation of the aforementioned invention as applied to a plurality of MCUs (Master Control Units), a device essentially synonymous with aforedescribed SCUs (System Control Units) 302 except that MCUs are typically (but not necessarily) externally located master devices while SCUs may alternatively be formed as internal or external master devices. However, the use of the term of MCU versus SCU should be considered to be interchangeable for the purpose of the present invention. The following describes an exemplary system and method for solving the potential problem of a plurality MCUs and their associated implantable medical (typically slave) devices, e.g., BIONs (wherein BION® is a registered trademark of Advanced Bionics® Corporation of Sylmar, Calif.), co-existence on a common communication channel and the associated potential interference between these devices due to their sharing of the common resource, i.e., the common communication channel.

B) Assumptions

The following are the set of assumptions for this exemplary solution:

1) A master device will hear another master device soon enough to take action before interference will occur. In the rare situation when a master device suddenly gets its signals interfered with by another master device, a pre-programmed "escape" plan will be immediately executed (see section D-7 for further details).

2) A BION can resynchronize to its master device even in the presence of randomly placed BPSK beacon messages.

3) Frame periods can be moved around. The master device's header and the BIONs can be shifted by any number of half slots, up to one full frame period.

4) A block of sufficient length will always be available for another system or any group of systems.

5) If Master Device A can't successfully receive Master Device B's beacon message signal, then Master Device B will not interfere Master Device A's normal MTB (Master to BION) operation.

6A) The Beacon Message Code has a processing gain, currently estimated at approximately +18 dB.

6B) The Message Code has a processing gain, currently estimated at approximately +9 dB.

C) Definitions

1) Serial Number—a 23 bit number provided by the factory for each MCU. Each master device has a unique identification code.

2) ID Number—a 25 bit number which includes the 23 bit serial number as its LSBs and two additional bits provided by the medical practitioner during system configuration as its MSBs.

3) Master Device N—a master device which is defined by the ID number N.

4) Block—a contiguous group of BION slots.

5) Slot—a 16 baud (symbol) wide space of time in the frame period where either part of the header, trailer, or BION receiving or transmitting can be located.

6) Acknowledge—the process by which one master device recognizes or provides a move permission to other master devices. A master device acknowledges by modifying its own wandering and/or trailer beacon messages.

7) Countdown counter—a software counter that is decremented by one for each frame period that passes where Master Device A can hear Master Device B but where Master Device B does not acknowledge Master Device A when Master Device A's ID number is greater than Master Device B's ID number.

8) Count—the current value of the countdown counter.

9) Open—refers to either a slot or a block of slots that are not being used by any other master device that can be presently heard.

10) Move—refers to a shift in time of a master device's header, trailer, and occupied BION slots.

11) Downlink—the first half of the frame period (slot numbers 1 to 864) which is allocated for MCU transmissions to the BIONs.

12) Uplink—the second half of the frame period (slot numbers 865 to 1728) which is allocated for the BION's transmissions to the MCU.

D) Control Basis (Rules)

The following are the operating rules for the MTM system. All components in the system preferably operate according to the following set of rules:

1) Each master device acts based on avoiding other master devices that it has recently heard, giving preference to the higher ID numbers as they are recognized.

2) ID numbers can be a concatenation of some weighted value and the factory programmed serial numbers (see sections C-1, C-2 for Serial number and ID number definitions). For example, if we want to see that the system with the longest time between BION communications wins, then the number of skipped slots could become the 2 most significant bits of the ID number. A master device ID cannot be changed in the field and/or during normal operating conditions. The ID is factory set and the weighted value is determined by the medical practitioner.

3) Each master device will assign its BIONs to a block of time slots so that they occupy a contiguous set of slots that follow the header.

4) Each master device will transmit beacon messages with the following three beacon message sequences once per frame period.

a. Wandering Beaconing

Figure 19:
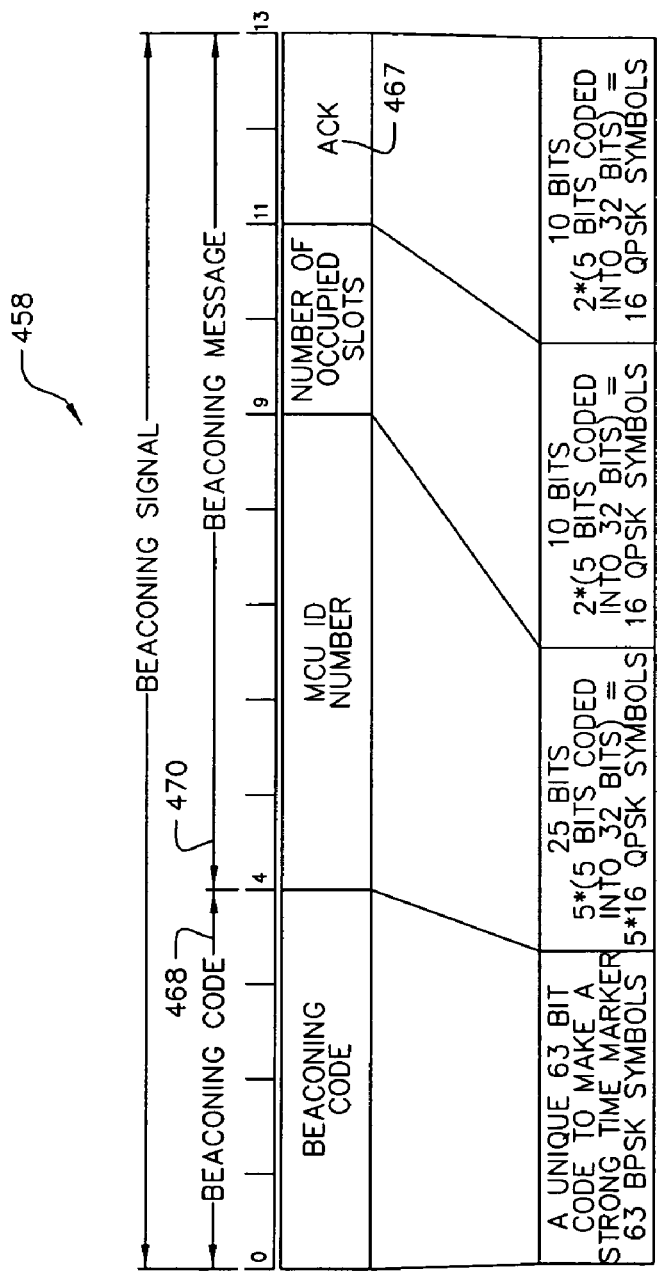
FIG. 19 shows an exemplary wandering beacon message having a heavily-coded marker code portion and a data portion which is preferably included in a selected set of predetermined locations throughout the frame period of FIG. 10.

An eleven BION slot wide beacon message sequence is illustrated in FIG. 19.

1) A unique 62 bit code is used to make a strong, i.e., heavily-coded, time marker code. This code is transmitted as 31 QPSK symbols to occupy 2 BION slots.

2) A field of 25 bits (5 BION slots) is used which contains the MCU ID number information.

3) A field of 10 bits (2 BION slots) contains the number of BION slots occupied by this system (2 BION slots).

4) A field of 10 bits (2 BION slots) is used as an acknowledgment (ACK) field (see section D-5 for further information on the acknowledgment method).

Sixteen slots ($S_{15}$-$S_0$) will be universally denoted as possible wandering beacon message transmission starting points. Each $S_i$ indicates a possible starting location for the wandering beacon message code. The specific ($S_{15}$-$S_0$) numbers are specified in Table I.

From the sixteen possible starting slots, one $S_i$ is selected by the use of a pseudorandom number generator for each frame period. The possible starting slots are rotated through so that each one is used before any one is reused, ensuring that all are used equally. If the use of any slot would interfere with this or any other system, that slot will be eliminated from consideration until the conflict is resolved. The possible starting locations for the wandering beacon messages described above were chosen in such a way that the location of the remote master device's "start of frame" can be precisely determined from hearing at least two wandering beacon messages located in two unique positions.

b. Header Beaconing

Figure 17:
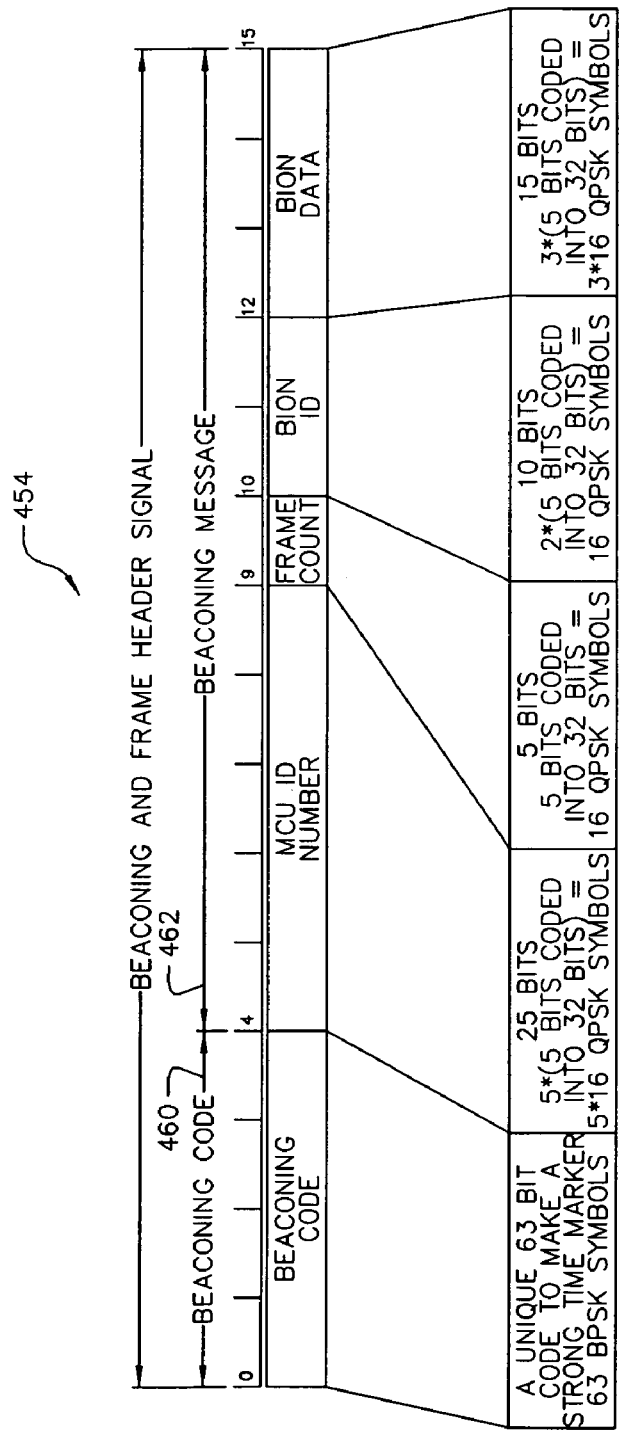
FIG. 17 shows an exemplary header beacon message having a heavily-coded marker code portion and a data portion which is preferably included as the first portion of the system control time period of FIG. 10.

An eleven BION slot wide beacon message sequence serves as the frame period's header. The header beacon message structure is illustrated in FIG. 17.

1) A unique 62 bit code to make a strong time marker code. This code is transmitted as 31 QPSK symbols to occupy 2 BION slots.

2) A field of 10 bits (2 BION slots) contains the BION ID information.

3) A field of 25 bits (5 BION slots) contains the Master Device ID number information.

4) A field of 5 bits (1 BION slot) contains the Plan information.

5) A field of 5 bits (1 BION slot) contains the Frame Number information.

The header beacon message's starting location is the very first slot of the frame period (slot 1 in the downlink half of the frame period).

c. Trailer Beaconing

Figure 18:
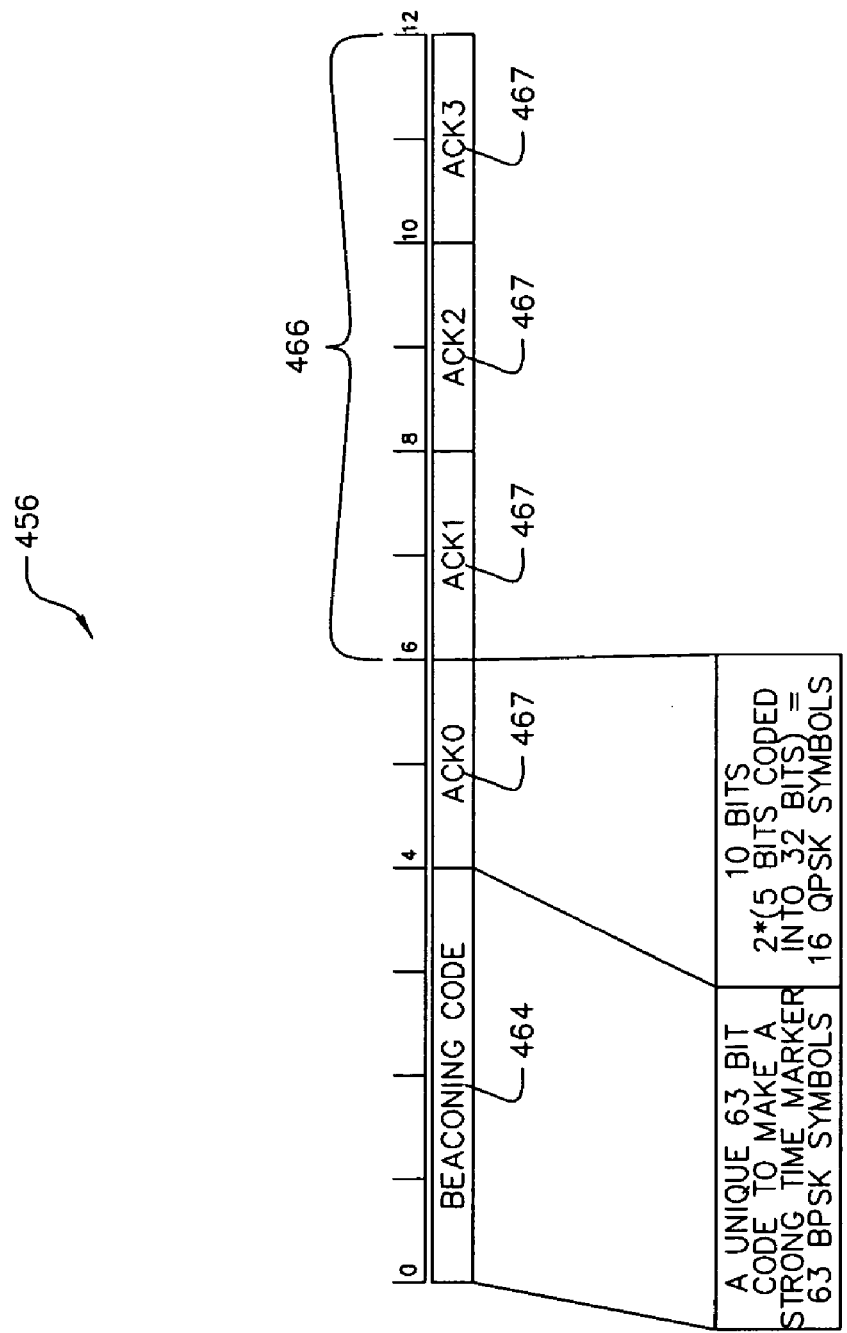
FIG. 18 shows an exemplary trailer beacon message having a heavily-coded marker code portion and a data portion which is preferably included as the first portion of the response data time period of FIG. 10.

An eleven BION slot wide beacon message sequence is illustrated in FIG. 18.

1) A unique 62 bit code to make a strong time marker code. This code is transmitted as 31 QPSK symbols to occupy 2 BION slots.

2) A field of 10 bits (2 BION slots) contains acknowledgment information (see section 5 for further acknowledgment method information). This field repeats itself 4 times.

3) A field of 5 bits (1 BION slot) is used in an unused period. Preferably, the MCU transmitter is off during this period.

The trailer beacon message's starting location is the very first slot of the frame period's uplink half.

5) The acknowledgment (ACK) method is based on three categories:

a. No other master device heard—in case a master device is not aware of any other master device in its presence, it will transmit a unique universal code as part of its wandering and trailer ACK fields.

b. Interference ACK—this category includes the cases in which Master Device A is signaling that it is aware of the presence of Master Device B. The Interference ACK is done by Master Device A transmitting the LSB bits of Master Device B's ID number in its wandering and trailer beacon ACK fields.

c. Move Permission ACK—this category includes the case of a conditional move as described in section 7 herein. The Move Permission ACK is done by Master Device A transmitting the 10 LSB bits of Master Device B's ID number in its wandering and trailer beacon ACK fields.

The wandering ACK field data will stay constant and is transmitted for 10 successive frame periods to allow the remote master device to have at least 8 successful integrations (in order to gain a high processing gain, currently estimated at approximately +9 dB). The beacon message code is changed each time the ACK field data changes (switching between two different codes).

The trailer ACK field data will stay constant and is transmitted for 2 successive frame periods. Assuming the trailer ACK field is duplicated four times in the message and is transmitted for two successive frame periods, the remote master device is able to integrate the information 8 times in order to gain a high processing gain, currently estimated at approximately +9 dB.

6) When Master Device N realizes that Master Device M's slot assignment will interfere with Master Device N's slot assignment, Master Device N will act as follows:

a) When N>M,

Master Device N will initialize a countdown counter to establish the number of frame periods that Master Device M was heard without hearing an acknowledge signal from Master Device M. When and if Master Device N realizes that Master Device M acknowledged Master Device N, then the countdown process will be terminated. If instead the countdown counter reaches zero, then Master Device N will take action to avoid interference by an act of moving according to subsections 1 and 2 herein, even though Master Device N has a higher ID number.

1. When Master Device N is not aware of Master Device J and where J>N, Master Device N will move to a block of sufficient length prior to the header of Master Device N. This process proceeds by first looking for an open block beginning with the slot preceding the header for Master Device N. If an open block of suitable length cannot be found there, the search repeats with the slot preceding that slot. This process continues until a suitable block is located. Before making a move, Master Device N will verify that Master Device M will not be taking action (and has not taken action) to eliminate interference with Master Device N.

2. When Master Device N is aware of Master Device $J_i$, where $J_i$>N, for i=1, 2, 3 . . . , Master Device N will set up a countdown process. While the countdown process is occurring, Master Device N will continue listening to all Master Devices $J_i$ beacon messages seeking for an ACK with a Master Device N ID number from each of them. Master Device N will move after it hears all Master Devices $J_i$ acknowledge or the countdown has expired. Before making a move, Master Device N will verify that Master Device M will not be taking action (and has not taken action) to eliminate interference with Master Device N. Master Device N will move to the block prior to the header of Master Device N of sufficient length. This process proceeds by first looking for an open block beginning with the slot preceding the header for Master Device N. If an open block of suitable length cannot be found there, the search repeats with the slot preceding that slot. This process continues until a suitable block is located.

b) When N<M,

1. When Master Device N is not aware of Master Device J and where J>N, Master Device N will move to the first open block of sufficient length after Master Device N's present location. This process proceeds by first looking for an open block beginning with the slot after the first word of the header of Master Device N. If an open block of suitable length cannot be found there, the search repeats with the slot after that slot. This process continues until a suitable block is located. Before making a move, Master Device N will verify that Master Device M will not be taking action (and has not taken action) to eliminate interference with Master Device N.

2. When Master Device N is aware of Master Device $J_i$ and where $J_i$>N, for i=1, 2, 3 . . . , Master Device N will set up a countdown process. While the countdown process is on, Master Device N will continue listening to all Master Devices $J_i$ beacon messages seeking for an ACK with Master Device N ID number from all of them. Master Device N will move when it hears all Master Devices $J_i$ acknowledge or the countdown expires. Before making a move, Master Device N will verify that Master Device M will not be taking action (and has not taken action) to eliminate interference with Master Device N. Master Device N will move to the first open block of sufficient length after Master Device N's present location. This process proceeds by first looking for an open block beginning with the slot after the first word of the header of Master Device N. If an open block of suitable length cannot be found there, the search repeats with the slot after that slot. This process continues until a suitable block is located.

7) During normal operation, the MCU will communicate an alternative "escape" plan to its associated BIONs in case of a communication loss between them due to an unexpected strong master device transmission interference. The MCU will communicate a specific pre-defined move location to all of its BIONs. This planned move is stored at the BION and will be executed by each BION in case it lost communication with its master device and it cannot re-locate or re-acquire it again. This situation might occur in the rare case when a MCU suddenly and unexpectedly finds itself interfered with by another master device without going thought the normal Interference Analysis procedure.

8) A master device will synchronize its internal oscillator to the highest ID number master device it is aware of. The remote master device's fixed header or trailer beacon message signals may serve as the time marker code. The motivation for this action is to minimize the frequency drift effect that might increase the number of required moves.

E) Content and Overview of the Control Blocks/State Machine Descriptions

This section contains the following sections and descriptions:

1) Section F describes the state machine sequence. This section graphically describes the sequence of events during operation of the MTM subsystem. A general skeleton as well as a detailed state description is described.
2) Section G describes the MTM software internal process. Some state machine internal processes are presented in this section.
3) Section H describes the database structure, definitions, maintenance and bookkeeping processes. This section concentrates on the MTM database which is the main input to the MTM software routine. The database reflects the external environment in which the MCU functions.
4) Section I describes the functions and procedures that give other software access to the MTM functions and data. The MTM software is a spawned process of the MCU software. This section contains a description of the interface between the MCU main software and the MTM software to detail the processes such as a Local Master Move, a local master device beaconing, and a data transfer between the two software routines.

F) State Machine Sequence

Figure 21:
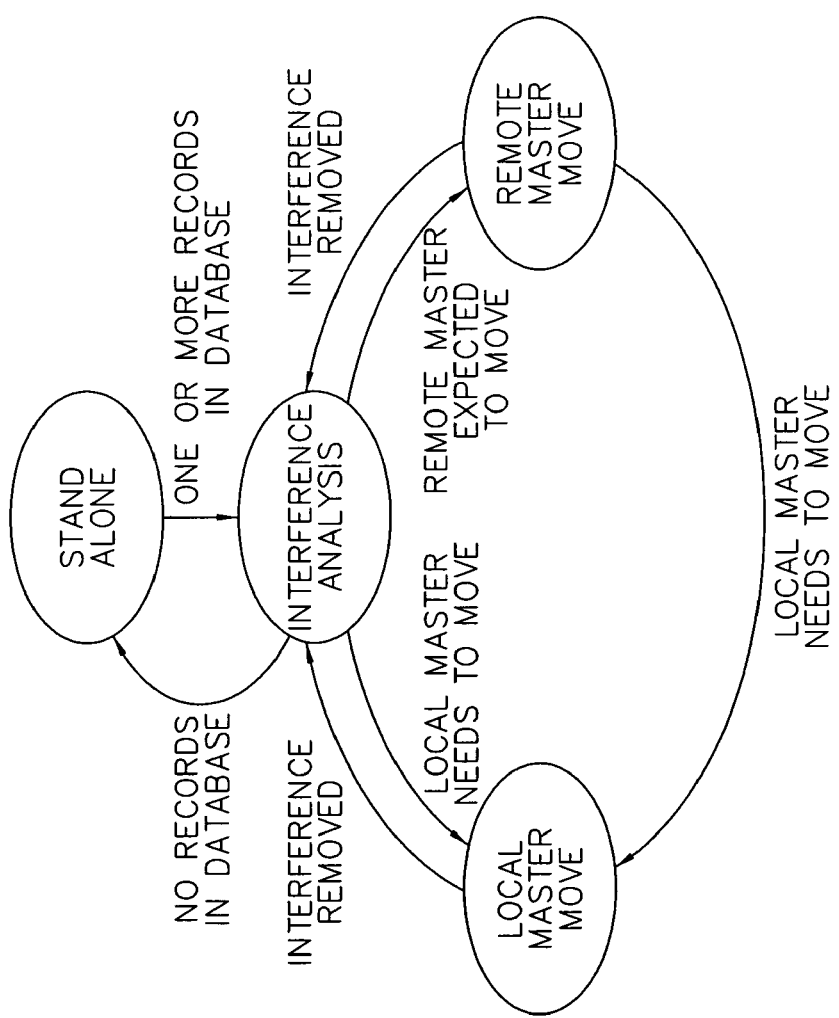
FIG. 21 shows the MTM state machine skeleton (a simplified version of that previously shown in FIG. 16).

The MTM state machine skeleton (a simplified version of that previously shown in FIG. 16) is illustrated in FIG. 21. As presented, the Interference Analysis (IA) state determines if interference is occurring between the local master device and one or more remote master devices. Based on the interfering master device's ID number, a decision is made between which action (local or remote master device move) should be taken. The Stand Alone state represents the mode in which the MCU is not aware of any other MCU system in the area and functions without interfering with or receiving interference from another master device. The Local Master Move and Remote Master Move are describing states in which an action needs to be taken due to detected interference.

1) The Stand Alone State

In this state, the system is checking the database to see that no remote master devices have been heard. If a remote master device is heard, a transition to the interference analysis state is made. Otherwise, the system remains in this state. While the MTM system is in the Stand Alone mode, it will transmit a unique universal code as part of its wandering and trailer ACK fields.

2) The Interference Analysis (IA) State

Within the IA state, the database remote master device records are analyzed to determine possible interference between the local master device and one of the remote master devices. If interference is detected, the MTM software will identify which move (remote or local master device) should be taken.

3. Local Master Move State

Figure 22:
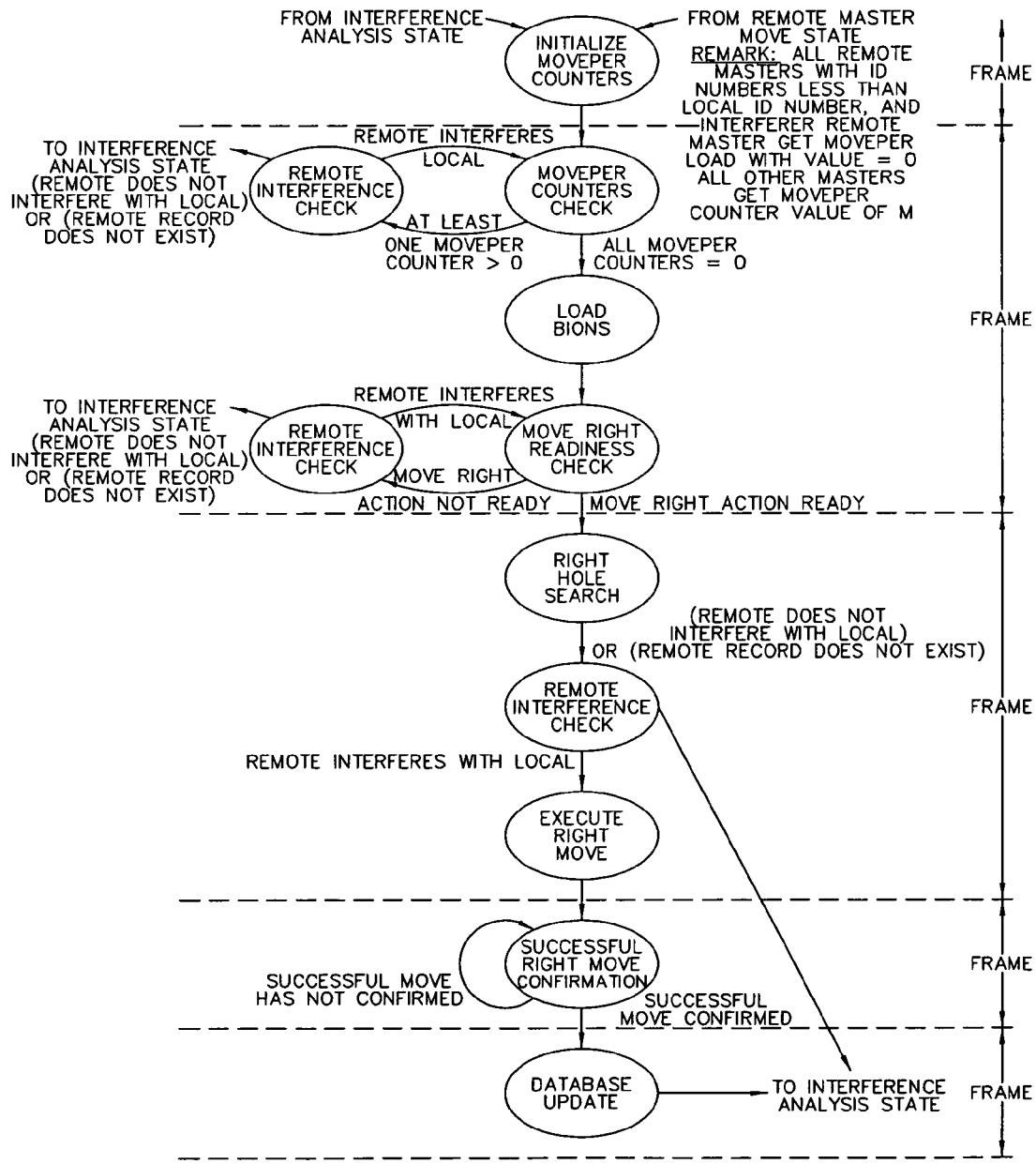
FIG. 22 illustrates the Local Master Move sequence used in an exemplary implementation.

If interference is detected within the IA state and the interfering master device has an ID number which is greater then the local master device ID number, then the local master device must move. This move will be to the right of the local master device's current location. If there are other remote master devices in the database that have an ID number greater than the local master device ID number, then permission to move needs to be granted prior to moving the local master device. Once permission has been granted, the MTM software communicates the BION move to the MCU software. A detailed description of this process can be found in section I-1 herein. FIG. 22 illustrates the Local Master Move sequence.

4. Remote Master Move State

Figure 23:
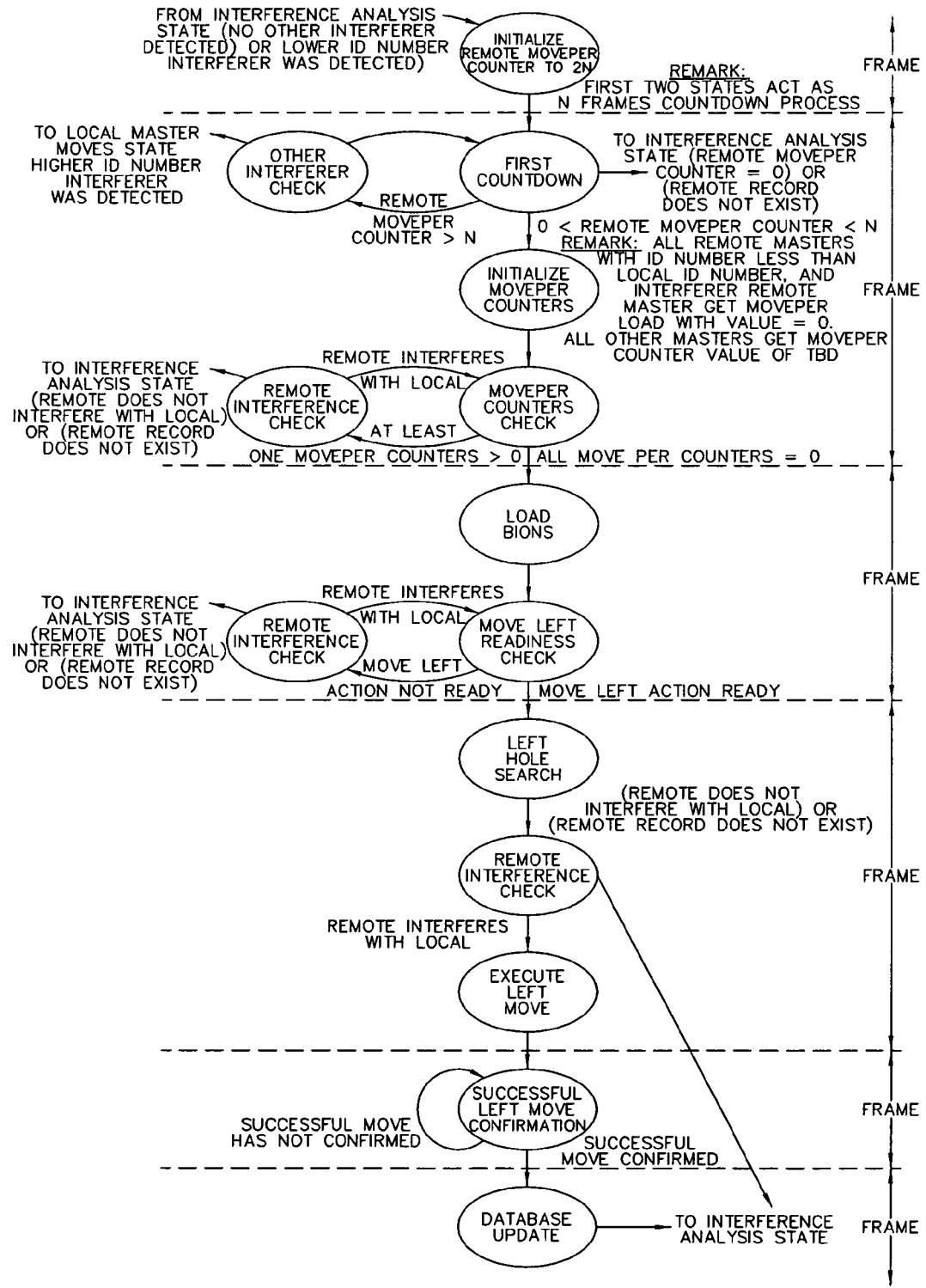
FIG. 23 illustrates the Remote Master Move sequence used in an exemplary implementation.

If interference is detected by the IA state and the interfering master device has an ID number which is less than the local master device ID number, then the local master device is expecting the interfering master device to move. If such a move doesn't happen within a certain time period, then the local master device will move in order to avoid the interference. In this case, the Local Master Move will be to the left of the local master device's current location. If there are other remote master devices in the database that have an ID number greater than the local master device ID number, then permission must be granted to the local master device prior to moving. Once move permission has been granted, the MTM software communicates the BION move to the MCU software. A detailed description of this process can be found in section I-1 herein. FIG. 23 illustrates the Remote Master Move sequence.

G) MTM Software Internal Process Descriptions

The following are descriptions of the main processes of the MTM operation. The sequencing of the procedures is controlled by the state machine.

1) Procedure to Search the Database for a New Hole
When a move of the local master device is called for, the database must be searched for a hole or opening of sufficient length that will not interfere with other master device's positions in the record. There are two procedures to perform this operation. One procedure starts at the beginning of the current frame period and checks position in successively higher BION slots until an opening is found. This is called a right search. The other procedure starts at the end of the frame period and searches successively lower BION slots. This is called a left search.

a) Right Hole Search

The first step to a right search is to build a temporary version of the database. This version contains only two fields for each record. The first field is the start position from the original database and the second field is the end position. Each start position is checked to determine if it lies in the first half of the frame period. If not, one half of the frame period length is subtracted from the start and stop positions to align the remote master device's position in the first half of the local MCU's frame period (this step is called "mapping"). Each position in each record is adjusted to slot align the data from the raw baud aligned data. The process will take into account all partially filled slots by treating them as being completely filled.

Once the database is created, it is sorted in ascending order by the start position of each record. After a sorted database is prepared, the records are collapsed by coalescing records that overlap. The end of the last record is then compared to one half of the frame period length. If the end exceeds that value, either the first record will have its start value adjusted to zero or a new record will be inserted at the beginning of the database to map these occupied slots that are after the end of the mid frame period to the start of the frame period. What remains lists the start and end of each occupied area of the frame period referenced to the local MCU.

Figure 24:
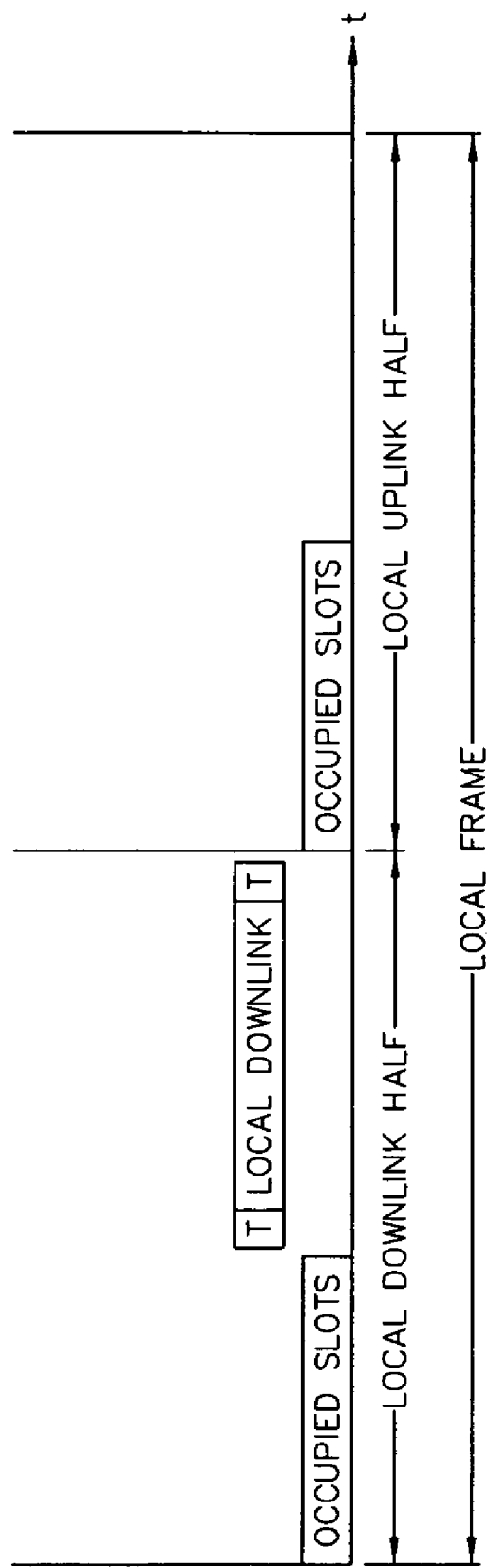
FIG. 24 illustrates a timing diagram for the MCU Frame Synchronization procedure used in an exemplary implementation.

The search is now conducted by checking the size of the opening between each pair of records remaining in the database beginning with the end of the first record and the start of the second record. If this gap is sufficiently large to allow the master device +2T (T is a guard region allowed on each end of the local master device's occupied slots) additional slots to move into, the start position of this opening is returned to the calling function. If the gap between these records is not large enough, the gap between each successive pair of records is tested until a suitable position is found. See FIG. 24 and section G (MCU Frame Synchronization procedure) for further information about T.

b) Left Hole Search

The first step to a left search is to build a temporary version of the database. This process is identical to the same process in the Right Hole Search which was described in section (a) above. The created database is sorted in ascending order and processed in an identical way as for the Right Hole Search. The search is now conducted by checking the size of the opening between each pair of records remaining in the database starting with the end of the next to the last record and the start of the last record. If this gap is sufficiently large to allow the master device +2T additional slots to move into, the position starting at the first occupied space of the record following this gap minus the necessary space to fit this master +2T additional slots is returned to the calling function. For example, if the master requires 104 slots and T=10 and the record following this gap starts at 1528, then the returned value is 1528−(104+2*10) or 1404. If the gap between these records is not large enough, the gap between each successive pair of records is tested until a suitable position is found. The order for the record search continues with the third from the last record and the second, then the fourth from the last and the third from the last, and so on.

Figure 25:
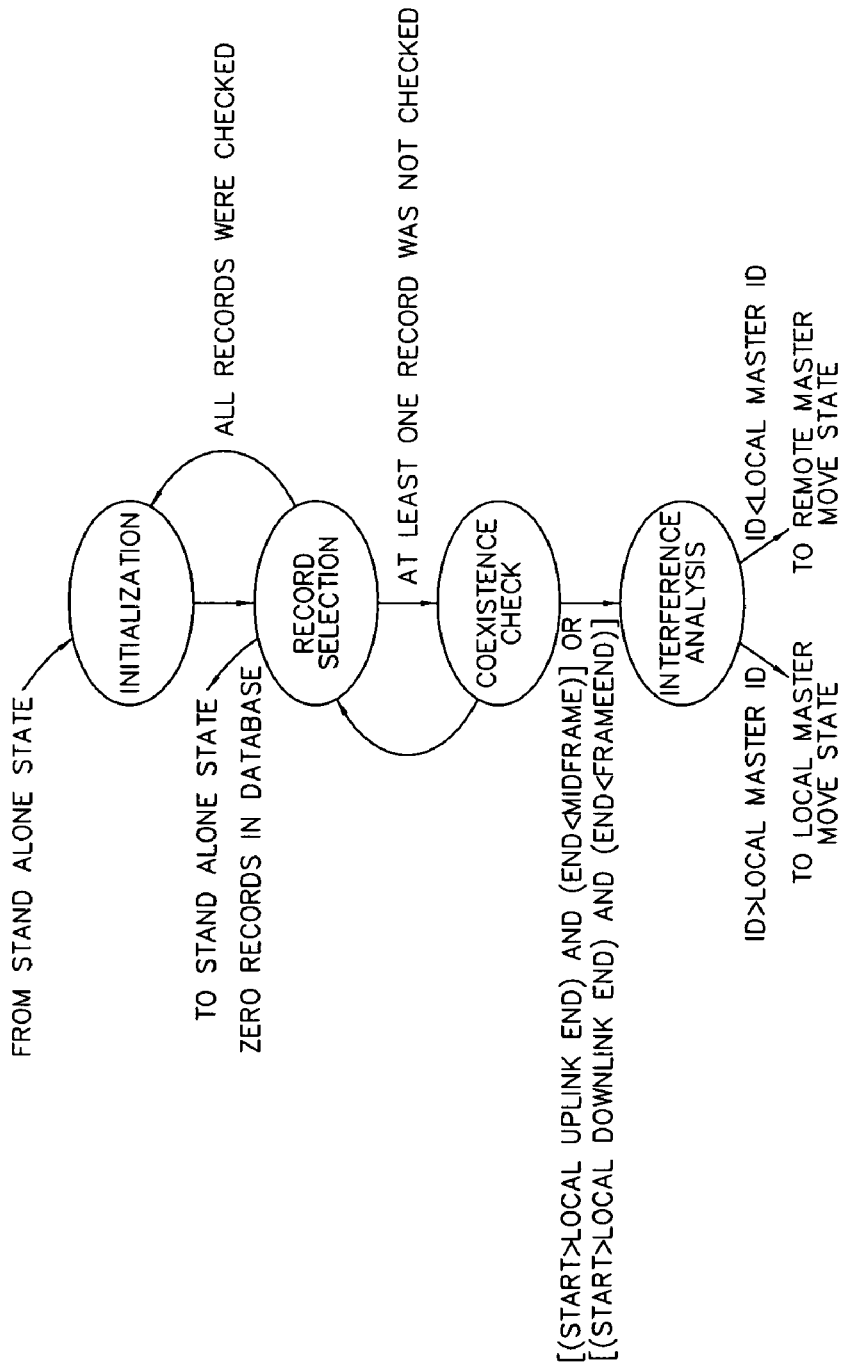
FIG. 25 illustrates a flow chart for the Local Master Move procedure used in an exemplary implementation.

2) Procedure for Interference Analysis Between the Local and One of the Remote Masters The state machine analyzes the data in the database of remote master devices checking for possible interference. The search is conducted in reverse ID number order and terminates when the first interfering record is found. The ID number from the interfering record is returned. If all records are searched and no interfering records are found, zero is returned. The process is as follows. First, the first record in the database is accessed. The value in the start field for that record is checked against the last baud location used by the local system for each the downlink and the uplink portions of the frame period. If the start is less than this value in either half of the frame period, the record is determined to be interfering and the search terminates. Otherwise, the value from the end field of that record is checked against the end of the downlink and uplink portions. If the end is greater than this value in either half of the frame period, again the record is determined to be interfering and the search terminates. If the first record does not violate any of the interference conditions, the next record is checked in the same way. Each successive record is checked until all records have been checked or until an interfering record is found. If interference is found, a new state is entered on the next frame period. That state depends on the ID number of the interfering master device. Interference with a lower ID number master device will cause a transition to Remote Master Move whereas interference with a higher ID number master device will cause a transition to the Local Master Move procedure. FIG. 25 illustrates a flow chart for this procedure.

3. Initialize Move Permission Counters

In this procedure, the permission counters (MovePer) in each record of the remote master device database is set to the number of frame periods to wait for move permission. The value is set to zero for all records where the remote master device's ID number is smaller than the local master device's ID number and is also set to zero for the record of the master device which is the cause of the interference. All other records (those with a greater ID number that aren't the cause for the move) are set to M, where M is the number of frame periods to wait before a forced move takes place even if permission is not granted by those remote master devices.

4. Remote Interference Check

Remote Interference Check is similar to Interference Analysis above. The difference is in what happens on the exit condition. If interference ceases, a transition to Interference Analysis will occur at the start of the next frame period. Continued interference will cause the system to remain in this state until other conditions (MovePer Counters) force progression to other states.

5. MovePer Counters Check

Each frame period that passes the move permission counters are updated in each record of the database. This procedure inspects the value of the counters in all records. There are two possible outcomes. If all records contain a zero, move permission is granted. If any record does not contain a zero in the move permission counter field, permission is not granted.

6. Load BIONs

This procedure is a call to an interface procedure in the main software. When the call is executed, the main software is told a move is imminent and it must prepare the BIONs for the move.

7. Move Right Readiness Check

When the MTM software executes the Load BIONs procedure, the main MCU software responds by updating a flag indicating the progress in informing the BIONs of the move.

The MTM software monitors that progress to see when it is complete. Not until the main MCU software determines that the BIONs are ready to move does the MTM software proceed to tell the MCU software to perform the move. It waits in this state until the BIONs are ready.

8. Execute Right Move

When the main MCU software has reported that all BIONs are ready for the move and a suitable location is found, the MTM software will issue a call to the procedure that tells the main MCU software to perform the move. That call makes up the Execute Right Move procedure.

9. Successful Right Move Confirmation

This procedure waits for confirmation from the main MCU software that the move has occurred. Once the header is moved, the move is considered complete.

10. Database Update

This procedure (routine) is called after a move is confirmed. After the move is complete, the database needs to have all pointers updated. This procedure updates start pointers, end pointers, and old start locations (OSL) pointers. Records are adjusted reflecting the new starting position of the local master device's frame period (header). This is the final step in executing a move.

11. Initialize Remote MovePer Counter to 2N

A counter is setup to countdown the waiting time while the local master device waits for the remote master device to move. The count is from 2N to N so the waiting time is not more than N frame periods.

12. First Countdown

This procedure determines if the local master device has waited too long for the remote master device to move. If the MovePer counter is less than M (but not zero), the local master device proceeds as though the remote master device will not move. If the count does reach zero, this signifies that the remote master device has acknowledged the local master device and this system returns to the Interference Analysis state. This refers to the check occurring at the top of FIG. 23.

13. Other Interferer Check

This procedure is very much like the Remote Interference Check with the exception being the exit action. In this procedure, a transition to the Local Master Move state occurs if interference with a remote master device having a higher ID number is found. If the interfering remote master device acknowledges the local system, the system returns to the Interference Analysis state.

14. Move Left Readiness Check

The actions in this procedure are identical to Move Right Readiness Check.

15. Execute Left Move

The actions in this procedure are identical to Execute Right Move.

16. Successful Left Move Confirmation

The actions in this procedure are identical to Successful Right Move Confirmation.

17. Wandering Beacon Message Transmission Starting Location ($S_i$) Generator

The action in this procedure is to determine the wandering beacon message starting point for future frame periods. As described above, there are 16 universal pre-assigned possible locations for the starting point of the wandering beacon messages. Based on an algorithm, one possible location out of the 16 possibilities will be chosen for each future frame period. The algorithm will not allow a location ($S_i$) that will interfere with MTB communications of either the local master device or a known remote master device. The 16 universal pre-assigned possible starting locations for the wandering beacon message transmissions are listed in the aforementioned Table I.

18. Wandering and Trailer Beacon Messages Transmission Generator

The action of this procedure is to determine the future transmissions of both the wandering and trailer beacon messages. The wandering and trailer ACK fields are independent. There is a need to determine the future frame period's ACK transmission messages as well as the relative marker code for the wandering message (as it is switches between two codes every time there is a change in the ACK field).

19. Wandering Beacon Message to Database Index Correlator

This procedure gets as an input a wandering beacon message starting location and returns as an output a list of possible database handles (usually one handle) that could be matched (associated) to this particular wandering message. If none of those messages match, this procedure creates a new record in the database and returns a handle to the new record as an output.

20. Header or Trailer Beacon Message to Database Index Correlator

This procedure gets as an input a header or trailer beacon message starting location and returns as an output a list of possible database handles (usually one handle) that could be matched (associated) to this particular received beacon message. If none of those messages matches, the procedure creates a new record in the database and returns a handle to the new record as an output.

21. Escape Plan Generator

During normal operation the MCU will communicate to its associated BIONs an alternative "escape plan" in case Master to BION (MTB) communication is lost due to an unexpected and strong interfering master device's transmission. The MCU will search and locate an available "escape hole" of sufficient size for the local system which will not interfere with or get interfered with by other remote master devices. This hole will be searched in the area of about ¼ frame period from the local master device (for example, if the local master device occupies slots {0 . . . X} and {0.5 . . . 0.5+X} for downlink and uplink halves respectively, then the "escape hole" search will begin in the area of {0.25.0.25+X} and {0.75.0.75+X}).

The "escape hole" location validity is checked every 5 frame periods by the Interference Analysis (IA) procedure to ensure its availability as a possible "escape" location. The MCU will communicate this specific pre-defined move location to all of its BIONs. The planned move is stored by the BIONs and is executed by each BION in case it loses communication with its master device and cannot re-locate and re-acquire it again. This situation might occur in the rare case when a MCU suddenly and unexpectedly finds itself interfered with by another master device without going thought the normal Interference Analysis procedure describes above. The Escape Plan Generator procedure might update from time to time its assigned "escape hole" as a result of the communicated environmental conditions. Each time the "escape hole" location is changed, the MCU will communicate the new location to its BIONs.

22. MCU Frame Synchronization Procedure

This procedure will synchronize the local MCU frame period to another remote master device's frame period, preferably the fastest remote master device as determined by the relative measured drift rate. The local master device will be locked to the fastest remote master device only in case the remote master device has a faster clock. In other words, the local master device will lock to a master device in its database that has the most positive drift. The local master device frame period synchronization may be implemented as either one of the following two options: a) adjusting the MCU internal oscillator, or b) controlling the frame period timing mechanism.

As described in section I herein, the local MCU will calculate the drifting rate, in terms of bauds per frame period, for each one of the remote master devices in the database. In the database, an old position of the "start" field will be recorded as well as the number of frame periods passed since this record was taken. The software controlling the clock can access those values as well as the current "start" position and determine each remote master device's drift rate. The remote master device's drift rate is calculated by dividing the difference in bauds between the two known values of the "start" fields by the number of elapsed frame periods since the old start location (OSL) was recorded (see more details in section I herein). The software controlling the clock can access this data to determine how much shift is necessary in the timing. Once the drift rate of each remote master device is calculated, the local master device will synchronize its frame period to the fastest MCU if any MCU has a faster clock than the local master device. Facilities are included to reset the stored values of the old start location (OSL) and frame period count to erase the history and start a new drift measurement.

In order to reduce the possible need for a move due to a drift just after a completion of a move, a buffer between the two systems is added. The size of the buffer is T slots and it is added in front and after the end of the local master device's frame period (see FIG. 24 for further details). The 2T slots (T slots in front and T slots in the end) serve as guard regions so that when two master devices drift toward one another, the subsequent collision will be delayed for a few frame period times after the move had occurred. This method reduces the rate of collisions due to a drift.

23. Return to Nominal Clock Speed Procedure

This procedure will cause the local master device to return to its nominal clock speed if it was adjusted by the MCU Frame Synchronization procedure (see above). The local master device may have adjusted its clock speed in order to lock to a remote master device, as described above. In this case, this procedure will cause the local master device to slow its clock to its nominal clock speed. This procedure shall be called when the local master device returns back to the Stand Alone state (meaning the local MCU is not aware of any remote master device in its presence).

H) Database Structure, Definitions, Maintenance and Bookkeeping Process

The MTM database serves as the main input for the MTM state machine operation. The database is updated once per frame period just before the MTM state machine procedure is called to validate the assumption that the MTM operation is making decisions based on an updated database.

1. MTM Database Purpose

Each master device will maintain a dynamically updated database of other master devices (remotes) it is aware of. The database is updated constantly, i.e., each detected, e.g., heard, master device is documented and each master device that can no longer be heard will be removed from the database. The database will serve as the input for the MTM operation algorithm.

2. MTM Database Structure

Figure 20:
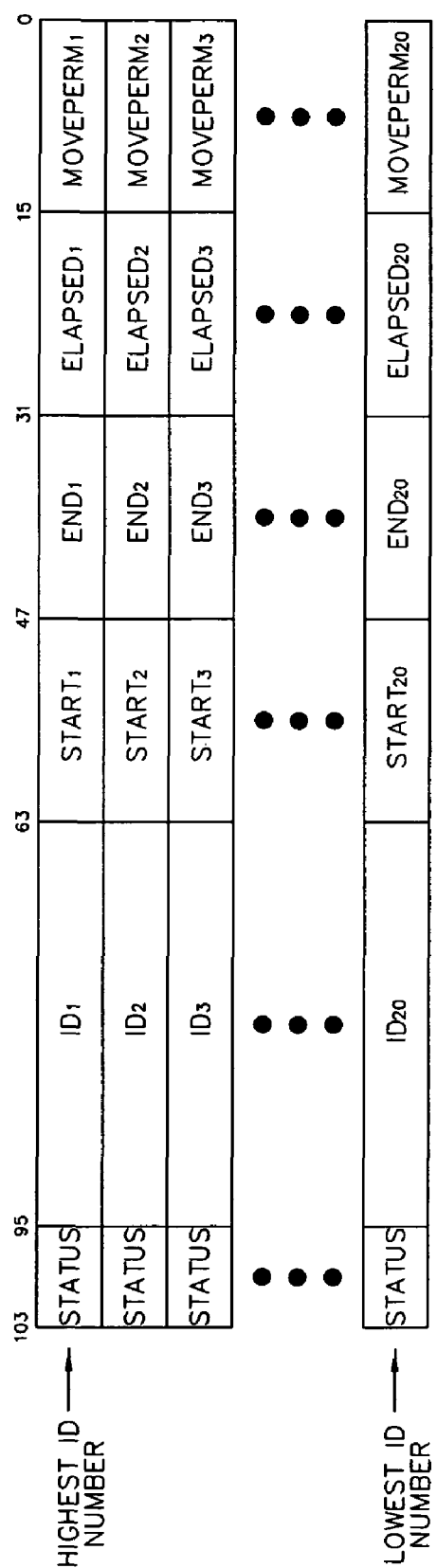
FIG. 20 shows an exemplary structure of the master to master database for accumulating and tracking the relative positions of the occupied time slots of the frame periods of remote master devices and their one or more associated slave devices.

The database is formatted as one record for each remote master device, e.g., a maximum of 20 records. The records are preferably organized in reverse ID number order. Each record is preferably comprised of eight fields as illustrated in the records of FIG. 20.

ID: System ID number—this number is stored as a 32 bit number where the 25 LSBs contain the data.

Start': Depending on LV flag value (see Status flags below), this field will hold the relative offset (in bauds) to header start for remote master device (LV='1') or relative offset to received wandering beacon message code (LV='0'). This value is a signed 16 bit number that indicates how many baud periods exist from the start of the header for the local master device to the start of the header for the remote master device of this record. See FIGS. 26 and 27 for more information. Start' values may vary between 0 and frame_end.

Start: Start=Start'−16*N. The N extra slots serve as reserved guard slots.

End': Relative offset to the last used downlink baud—this value is an unsigned 16 bit number giving the offset from the start of the header for this local master device to the last used baud in the downlink portion of the frame period for the remote master device of this record. See FIGS. 26 and 27 for more information. End' is always greater than Start'. Values for End' can exceed the frame period length.

End: End=End'+16*N. The N extra slots serve as reserved guard slots.

Elapsed: Elapsed frame periods since last heard—this 16 bit value indicates the number of frame periods that have passed since the remote master device of this record was last heard by the local master device. When this count exceeds some yet to be determined value, this record is purged from the database.

MovePer: Move permission count—this 16 bit value functions in holding off moves until permission is given by the master device of this record. The operation is as follows. When a move is required, this field is loaded with the count of the maximum number of frame periods that the local master device can wait before the move will be executed unconditionally. This value is loaded if the master device of this record meets two criteria. The first criterion is that the master device must have a greater ID number and the second criterion is that the master device of this record must not be the motivation for this move. For all other master devices, this field is set to zero. On each elapsed frame period, the count in this field is decremented until zero is reached. If (and when) the master device of this record acknowledges this local master device, this field is also set to zero. When all records contain zero in this field, the move is executed.

Figure 28:
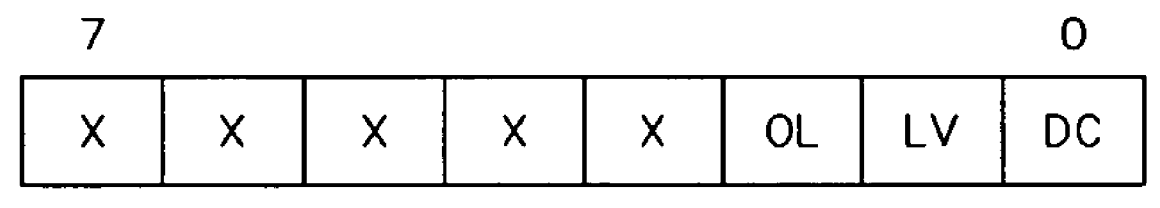

Status: This 8 bit field contains three status flags. The purpose of the status flags is to indicate the meaning and the validation of the data written in the other fields of this record. FIG. 28 illustrates the structure of the 'status' field.

a) DC (Data Complete) flag (bit 0 in the 'status' field), where:

DC='1'—signifies that data in record fields is complete and valid.

DC='0'—signifies that data in record fields is incomplete and not valid.

b) LV (Location Validation) flag (bit 1 in the 'status' field), where:
  LV='0'—signifies that the data in the 'start' field refers to the wandering beacon message starting location. In this case, the value written in the 'end' field is not valid.
  LV='1'—signifies that the data in the 'start' field is valid and indicates the remote master device's start frame period relative to the local master device's start frame period.
c) OL (Oscillator Locked) flag (bit 2 in the 'status' field). This flag indicates if the local master device is 'frame locked' to this remote master device. The local master device may be locked to one remote master device only.
  OL='0'—signifies that that the local master device is not 'frame locked' to this remote master device.
  OL='1'—signifies that that the local master device is 'frame locked' to this remote master device.

Frame Counter (FC):
  This 16 bit counter is reset upon transferring the start location to the OSL field. The counter's value is incremented by one for each elapsed frame period. The controlling software is able to reset this counter in conjunction with transferring the start location to the old start location (OSL field). The motivation for this counter is to support the remote master device's drift rate calculation in terms of bauds of drift per frame period. The FC provides the data for the number of elapsed frame periods between the old 'start' record and the current 'start' location record.

Old 'Start' Location (OSL):
  This signed 16 bit number will hold the relative offset to header start for the remote master device for the very first confirmed 'start' location. This value is adjusted each time either the local or the remote master device of this record make a move. This value can be read by the control software. Also, this value can be overwritten by the current start value in conjunction with resetting the Frame Count by the control software. The motivation for this value is to support the remote master device's drift rate calculation in terms of bauds of drift per frame period. This field provides the data for the old 'start' record which can be subtracted from the current 'start' location record and that difference is then divided by the FC counter.

Figure 26:
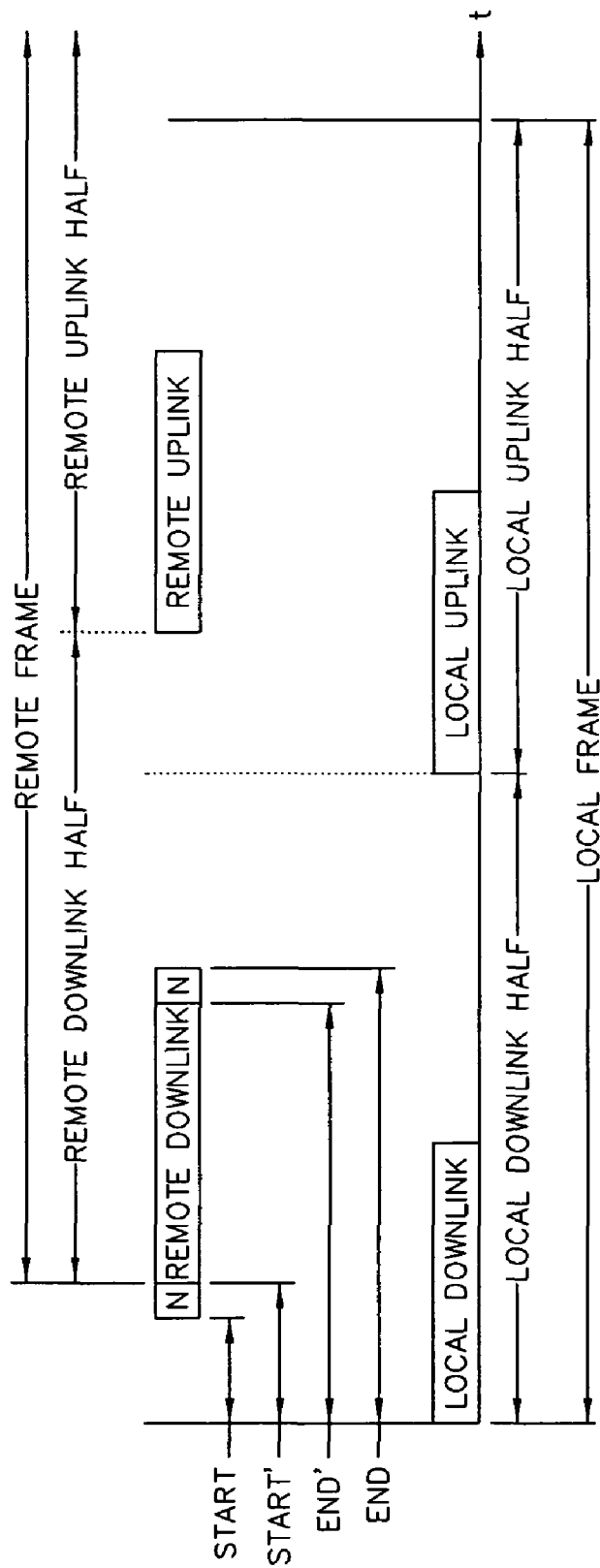
FIGS. 26 and 27 describe two representative possibilities for local and remote master devices relative positioning in an exemplary implementation.
Figure 27:
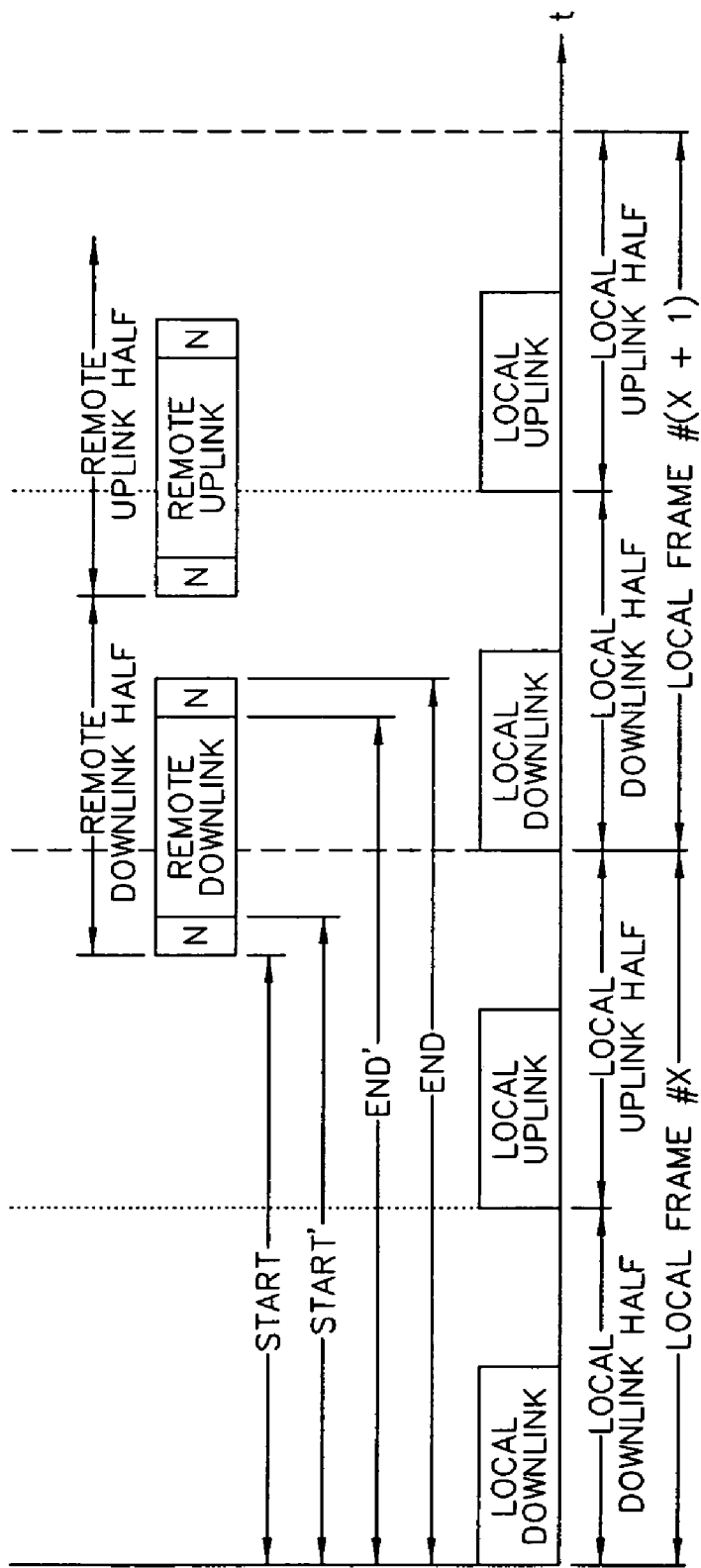

FIGS. 26 and 27 describe two representative possibilities for local and remote master device's relative positioning. In FIG. 26, the remote master device's downlink is located within the local master device's downlink section while in FIG. 27, the remote master device's downlink exists in the local master device's uplink section and end' is greater than frame_end. Note, these drawings are not shown drawn to scale.

3. Database Interface Procedures for MTM Operations

The database is modified under four conditions: 1) when new data is received from a remote master device, 2) when a remote master device has not been heard from for an extended period of time, 3) when the local master device executes a move, and 4) when the state machine is waiting for permission for a move. The procedure for modifying the database in each situation is discussed here.

New Data Received

Figure 29:
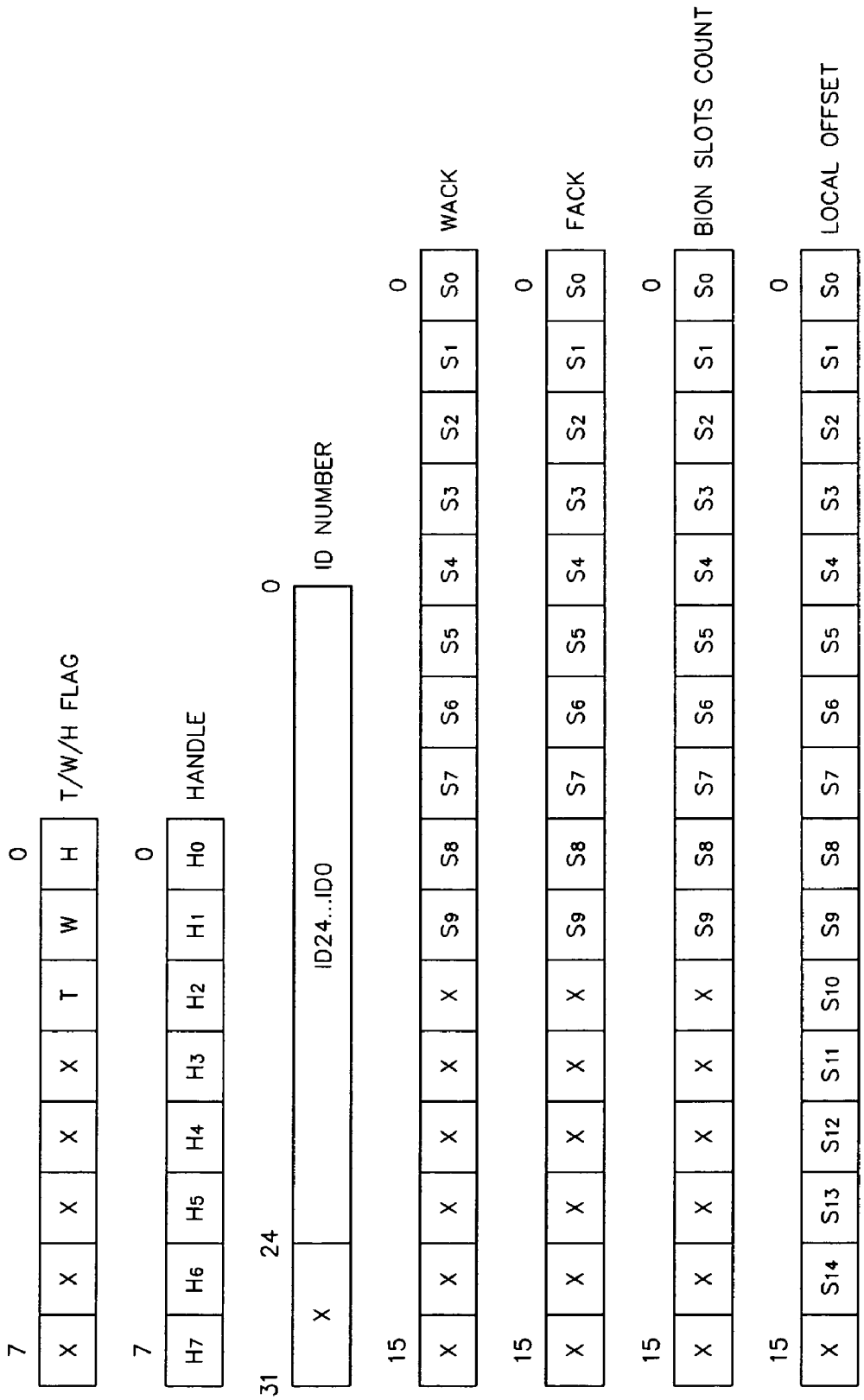
FIG. 29 illustrates the structure of the holding buffer structure used in an exemplary implementation.

The MCU receiver procedure gathers beacon messages from remote master devices and places the data into a holding buffer. Each received beacon message (header, trailer or wandering) is stored in a single holding buffer. The beacon message data processing procedure (called each frame period) performs the task of taking data from the holding buffer and transferring it to the remote master device database. The holding buffer structure is illustrated in FIG. 29.

The data that is in the buffer contains 7 fields of data as follows:
  T/W/H flag: an 8 bit field contains three flag bits: T, W and H. Each bit represents a received beacon message. A set bit indicates the source of the received beacon message, where:
    a) H='1', T='0', W='0'—header beacon message,
    b) H='0', T='1', W='0'—trailer beacon message,
    c) H='0', T='0', W='1'—wandering beacon message.
  ID number: a 32 bit long field where the least significant 25 bits contains data of the type identified by the ID flag field. The data in this field is valid for header or wandering beacon messages only. For trailer beacon messages, the data in this field should be ignored.
  BION slot count:
    a 16 bit long field containing a number from 1 to 844 that reports the number of slots the remote master device is using. This is valid for wandering beacon message only. For header or trailer beacon messages, the data in this field should be ignored.
  Local offset: a 16 bit long field is inserted by the MCU receiver procedure. This field identifies the start of message position in number of bauds from the start of header for the local master device.
  ACK: This 16 bit long field contains 10 bits of acknowledgment information received from a wandering or trailer beacon messages. For header beacon messages, the data in this field should be ignored.
  Handle: These 8 bits of data serve as a handle for the procedures described in section G.

Database Update Process

Based on the data type stored in the holding-buffer, the database is updated as follows. Based on the T/W/H flags, the following data fields are determined:

| T | W | H | ID Number | BION slot count | Local offset | ACK |
|---|---|---|-----------|-----------------|--------------|-----|
| 0 | 0 | 0 | X | X | X | X |
| 0 | 0 | 1 | Valid | X | Valid | X |
| 0 | 1 | 0 | Valid | Valid | Valid | Valid |
| 0 | 1 | 1 | X | X | X | X |
| 1 | 0 | 0 | X | X | Valid | Valid |
| 1 | 0 | 1 | X | X | X | X |
| 1 | 1 | 0 | X | X | X | X |
| 1 | 1 | 1 | X | X | X | X |

Figure 30:
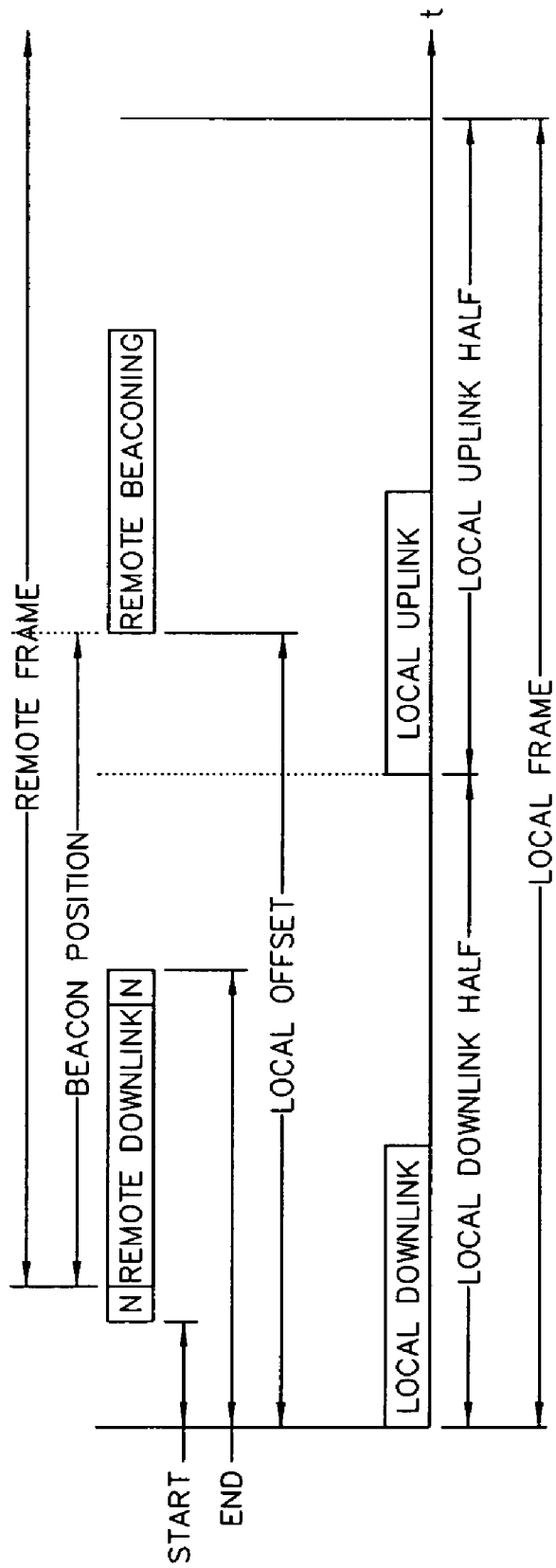
FIG. 30 illustrates an example of possible positioning between local and remote master devices in an exemplary implementation.

The BION slot count is multiplied by 16 and added to the sum of the start position and the header length in bauds to arrive at the end position for the remote master device. This value is relative to the local master device's start of header. Adjustments are made to provide for N slots of guard space as described above. FIG. 30 illustrates an example of possible positioning between local and remote master devices. Note that the length of the bars are not shown drawn to scale.

With this data, the database can be updated as follows. The first step is to determine if this remote master device is already in the database. The ID number is looked up in the database. If a match is found, the index record is updated as follows:

1. The existing and the new 'start' fields values are compared. If the difference between them is greater than 3 bauds, it is assumed that the remote master device had executed a move. When a remote master device move has been detected, the record's OSL value needs to be adjusted. The OSL is then adjusted by adding or subtracting the number of bauds moved for the old OSL value as called for by the direction of the move.

2. The other data from the message is used to update the record.

3. The DC flag (in the 'status field') is set to '1'.

4. The database elapsed counter field is set to the full value.

If this ID cannot be matched in any of the records, a new record is created and the DC flag (in the 'status field') is reset to '0'. The database is kept ordered by reverse ID number so the records with lower ID numbers are moved out by one record and the data from this message is used to fill in the new record. The elapsed field counter of this record is set to the full value and the MovePer counter field is set to the maximum value contained in that field for any of the other records if the ID number of this remote master device is greater than the ID number of the local MCU. If this unit has a smaller ID number than the local master device, the permission count is set at zero. The Frame Counter (FC) field is reset to zero. The 'start' value will be stored in the OSL field as well. Finally, the count of number of records is increased by one.

In case either ACK field contains the local master device's ID number, then the MovePer counter is set to zero. All new data records in the beacon message buffer are processed before exiting from the procedure.

Remote Record Purge

The procedure discussed above which updates records based on newly received beacon messages also performs another bookkeeping function. Once per frame period, at the end of updating all the records, it decrements the elapsed counter field of each record in the database. If this operation results in the elapsed counter being zero, the record is purged from the database. Purging a record causes all records after the purged record to move in by one record, overwriting the purged record. The count of the number of records is then decreased by one.

Adjust all Remote Offsets Due to a Local Master Move

Once a move of the local master device has been completed and the 'move completed' flag has been set, the database's records need to reflect the new 'start', 'end' and old start (OSL) locations relative to the new header of the local master device. The MTM will call the Database_Move_Update procedure. This procedure will get as an input the offset parameter and will update all remote records 'start', 'OSL' and 'end' in the database according to the following algorithm:

$$Start_{new} = \begin{cases} \text{frame\_length} - \text{Offset} * 8 + Start_{old} & \text{if Offset} > Start_{old} \\ Start_{old} - \text{Offset} & \text{if Offset} < Start_{old} \end{cases}$$

$$End_{new} = \begin{cases} \text{frame\_length} - \text{Offset} * 8 + End_{old} & \text{if Offset} > Start_{old} \\ End_{old} - \text{Offset} & \text{if Offset} < Start_{old} \end{cases}$$

$$OSL_{new} = \begin{cases} \text{frame\_length} - \text{Offset} * 8 + OSL_{old} & \text{if Offset} > OSL_{old} \\ OSL_{old} - \text{Offset} & \text{if Offset} < OSL_{old} \end{cases}$$

Note that Offset is given in terms of half slots and therefore needs to be multiplied by 8 in order to present it in terms of bauds (as 'start' and 'end' are presented).

Move Permission Counter Decrement

When the local master device is waiting for permission to move it will decrement the move permission counter (MovePer) in each record for each frame period that passes where permission is not granted for a move. This procedure checks the value in that field of the record and decrements it by one if the value is greater than zero.

I) Interfaces to Other MCU Software Systems

Figure 32:
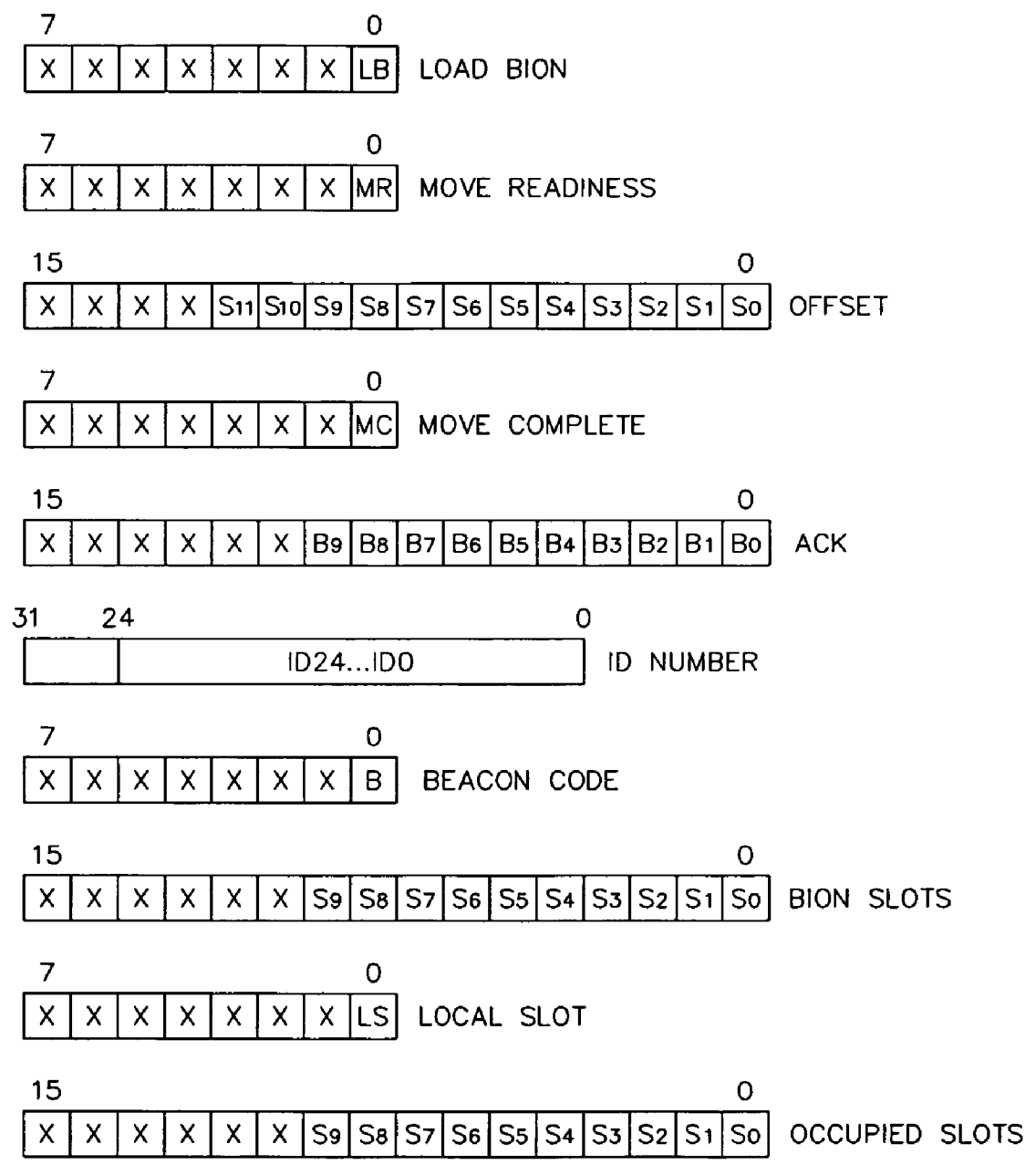

This section summarizes the interface between the MTM and MCU software. Defined are the interface's procedure names, and their input and output arguments. These procedures are shown in FIG. 31 and FIG. 32 shows the associated data structures.

1. Local Master Move Procedure

When a move is to occur, the state machine will communicate with the main MCU software to coordinate the move. Four procedures are involved in this coordination. The first procedure provides the main MCU software with move plan information. This procedure will set a flag that can be read by the main MCU software telling it a move is going to happen in the next few frame periods. The second procedure tells the main MCU software the move offset. The third procedure allows the MCU software to modify a flag telling the state machine that the BIONs are ready to execute a move. The fourth procedure modifies a flag to tell the state machine the move has executed. Before any other actions are taken, the MTM software clears the Move_Complete flag which may still be set from the last move.

Ready_Move: This procedure allows the state machine procedure to set a flag (the Load_BION flag) which is accessible by the MCU main software. When the main software detects that this flag is set, it will ready the BIONs for a move. The MCU main software will also clear the Execute_Move flag that may still be set from the last move. Once the BIONs are ready, the MCU software will notify the state machine software by calling the Ready_Move_Complete procedure.

Ready_Move_Complete:

This procedure is called by the main MCU software. When called, it sets a flag (the Move_Readiness flag) which is accessible to the state machine telling it the move can be executed. At this time, the MCU main software will also clear the Load_BION flag.

Execute_Move: This procedure is called by the state machine to tell the main MCU software to actually make the planned move. A single argument is provided in this call. The offset for the move is provided as a number of half slots. The main software will report this information to the BIONs which will in turn use this offset to set their new location in the frame period. At this time, the MTM software will also clear the Ready_Move_Complete flag.

Move_Complete: This procedure is called by the main software to set a flag (the Move_Complete flag) which is accessible to the state machine. This flag indicates the move has been executed and the local system is now operating in the new frame period location. The main procedure will clear the Move_Readiness flag before calling this procedure and this procedure will clear the Ready_Move_Complete flag. The MTM main software will then clear the offset provided by the Execute_Move call.

2. Local Master Device Wandering and Trailer Beaconing

A single procedure is called by the state machine once per frame period to set up the wandering and trailer beacon message transmissions for the next frame period. The actual wandering as well as the trailer beacon messages are sent by the main MCU software.

There are five arguments to this call to provide the main software with (1) the ID number to beacon message with, (2)

the number of BION slots used by the local system, (3) ACK field for wandering beacon message transmission, (4) ACK field for trailer beacon message transmission, and (5) the particular bit beacon message code for the wandering beacon message transmission.
  Beacon_Setup: This procedure is called by the state machine each frame period with four arguments to define the next wandering and trailer beacon message transmissions.
  Beacon_code: This Boolean value distinguishes between the two possible options for the marker code for the wandering beacon message code. The two possibilities for the marker codes to be used are as follows:
    B='0': type C3
    B='1': type C4
    The marker codes for the trailer beacon message transmission is fixed to be type C2. The marker code for the header beacon message transmission is fixed to be type C1.
  ID_number: This 32 bit number has 25 valid bits indicating the ID number that the local master device should transmit. The composition of this number is identified in the MTM solutions document.
  WACK: This argument is a 10 bit number generated by the ACK generator to be transmitted as part of the wandering beacon message transmission. The purpose of these 10 bits is to acknowledge a remote master device as needed.
  TAC: This argument is a 10 bit number generated by the ACK generator to be transmitted as part of the trailer beacon message transmission. The purpose of these 10 bits is to acknowledge a remote master device as needed.
  BION Slots: This 10 bit unsigned number represent the number of occupied slots used by the local master device. This number is to be included as part of the wandering beacon message transmission.
3. Number of Occupied Slots
  A procedure that is called by the state machine software and will return the number of slots used by the local master device. There are no arguments provided when calling this procedure.
  Local_slots: This procedure returns a number from 1 to 844 which is the number of slots occupied the BIONs of the local system. It has no arguments.
4. Reset Drift Registers:
  This procedure resets the FC and OSC fields for a specific index (i) in the database. When it is necessary to begin a new drift measurement, this procedure is called to clear the previous drift history. Once called, the FC field will be reset to zero and the OSL field will be written with the value of the current 'start' value. There is only one argument to this procedure call which is the record index (i) and (i) may vary between 0 and 19 and therefore will be represented as 5 bits.
5. Read Drift Rate
  This procedure, when called with parameter (i), returns two values:
    a. The FC field value for index (i).
    b. A signed difference between OSL and 'start' fields value for index i.
  The motivation for reading those values is to calculate the 'drift-rate' for record index (i) which is the difference between OSC and 'start' field divided by FC values as explained below. Note that all drift rate math calculations are preferably truncated and not rounded (the motivation for truncating is to avoid a run-away condition).

$$\text{Drifting Rate}(i) = \frac{\text{`OSC'} - \text{`start'}}{FC} \left[\frac{\text{bauds}}{\text{frame}}\right]$$

There is only one argument to this call which is the record index (i). The index (i) may vary between 0 and 19 and therefore will preferably be represented as 5 bits.

Accordingly, what has been shown is a system and method that enables a common communication channel to be shared between multiple systems of devices wherein, preferably, at least some of these devices are implantable. While the invention has been described by means of specific embodiments and applications thereof, it is understood that numerous modifications and variations could be made thereto by those skilled in the art without departing from the spirit and scope of the invention. For example, while the present invention is particularly suited to the field of implantable devices, the aforementioned protocol and method are also of value in non-implantable systems. It is therefore to be understood that within the scope of the claims, the invention may be practiced otherwise than as specifically described herein.

What is claimed is:

1. A method of enabling a plurality of systems (300-1, 300-2, 300-3) to communicate over a common communication channel wherein each system (300-1, 300-2, 300-3) is configured to enable communication during periodic and essentially temporally contiguous respective frame periods (409-1, 409-2, 409-3) determined essentially asynchronously by each said respective system (300-1, 300-2, 300-3) and having occupied temporal portions of each said frame period (409-1, 409-2, 409-3) comprised of transmission communication periods dedicated to each said respective system (300-1, 300-2, 300-3) and wherein each said frame period (409-1, 409-2, 409-3) has a start and an end that essentially spans the entire temporal bandwidth of said common communication channel, said method comprising the steps of:
  transmitting during each said frame period (409-1, 409-2, 409-3) from each said respective system (300-1, 300-2, 300-3), at least one type of beacon message (454, 456 or 458) having a respective unique heavily-coded beacon marker code portion (460, 464 or 468),
  wherein said step of transmitting at least one type of beacon message additionally comprises the step of transmitting at least one wandering beacon message having a moveable temporal offset from the start of its respective frame period;
  receiving beacon messages (454, 456, 458) by each of said systems (300-1, 300-2, 300-3) according to said heavily-coded beacon marker code portions (460, 464, 468) from other said systems (300-2, 300-3), (300-1, 300-3), (300-1, 300-2) that are within communication range;
  processing two or more of said received heavily-coded beacon marker code portions (460, 464, 468) of said respective beacon messages (454, 456, 458) to thereby determine the start of the frame period of another one of said systems; and
  determining which received beacon messages uniquely correspond to other said systems according to uniquely defined temporal displacements between said received wandering beacon messages.

2. The method of claim 1 wherein said transmitting during each said frame period at least one type of beacon message additionally comprises transmitting a data portion within said beacon message.

3. The method of claim 2 additionally comprising the step of integrating data portions from said received beacon messages that correspond to other said systems over a plurality of frame periods to thereby increase the receive sensitivity and the effective communication range and thereby facilitating extracting said data portions.

4. The method of claim 1 wherein said step of transmitting at least one wandering beacon message having a moveable temporal offset from the start of its respective frame period comprises selecting said temporal offsets from a predetermined set of temporal offset values.

5. The method of claim 1 wherein said step of transmitting at least one beacon message additionally comprises transmitting a wandering beacon message type having temporal offset values selected from a predetermined set of temporal offset values for at least two different frame periods and wherein said method additionally comprises the step of determining in part which received beacon messages uniquely correspond to other said systems according to uniquely defined temporal displacements between received beacon messages by comparing the differences between temporal offset values of wandering beacon messages from other frame periods according to said predetermined set of temporal values.

6. The method of claim 1 wherein said step of transmitting at least one type of beacon message additionally comprises the step of periodically ceasing transmissions from said systems to facilitate said steps of receiving beacon messages and integrating data portions from said received beacon messages.

7. The method of claim 1 wherein said systems are comprised of a master device and one or more associated slave devices that communicate with said master device during said frame periods determined by each said master device, said method additionally comprising the steps of:

calculating the relative temporal displacements of the frame periods of other master devices;

determining whether at least one of said systems may interfere with communications of another one of said systems and accordingly calculating a new temporal placement for the frame period of a selected one of said systems according to said received beacon messages; and causing said selected one of said systems comprised of a master device and one or more associated slave devices to temporally displace the start of its frame period to allow said occupied temporal portions of said selected one of said systems to be temporally interleaved with other occupied temporal portions of said systems across said common communication channel when said determining step has determined the potential for communication interference between two or more of said systems.

8. The method of claim 7 wherein each said master device has a unique identification code that is used within at least some of said beacon messages and said calculating step determines in part the new temporal placement for the frame period of a selected one Of said systems according to said received beacon messages and said unique identification codes.

9. The method of claim 7 wherein said calculating step determines in part the new temporal placement for the frame period of a selected one of said systems according to relative movement of the temporal placements of two or more sequential beacon messages received from another one of said master devices.

10. The method of claim 1 wherein the heavily-coded beacon marker code portion consists of:
    a 31 baud long string of QPSK symbols;
    a 63 baud long string of BPSK symbols; or
    a 62 bit code.

\* \* \* \* \*